(12) United States Patent
Oxborough et al.

(10) Patent No.: US 10,481,064 B2
(45) Date of Patent: Nov. 19, 2019

(54) BALLAST WATER MONITORING DEVICE

(71) Applicant: CHELSEA TECHNOLOGIES GROUP LTD, Surrey (GB)

(72) Inventors: Kevin Oxborough, Surrey (GB); John Attridge, Surrey (GB); David Andrewes, Surrey (GB)

(73) Assignee: CHELSEA TECHNOLOGIES GROUP LTD, Surrey (GB)

( * ) Notice: Subject to any disclaimer, the term of this patent is extended or adjusted under 35 U.S.C. 154(b) by 0 days.

(21) Appl. No.: 15/755,782

(22) PCT Filed: Aug. 10, 2016

(86) PCT No.: PCT/GB2016/052485
§ 371 (c)(1),
(2) Date: Feb. 27, 2018

(87) PCT Pub. No.: WO2017/037415
PCT Pub. Date: Mar. 9, 2017

(65) Prior Publication Data
US 2019/0033193 A1     Jan. 31, 2019

(30) Foreign Application Priority Data
Aug. 28, 2015 (GB) .................................. 1515370.3

(51) Int. Cl.
*G01N 1/00* (2006.01)
*G01N 15/06* (2006.01)
(Continued)

(52) U.S. Cl.
CPC .............. *G01N 15/06* (2013.01); *B63J 4/002* (2013.01); *C02F 1/00* (2013.01); *C02F 1/008* (2013.01);
(Continued)

(58) Field of Classification Search
CPC ................. G01N 1/2813; G01N 1/286; G01N 2001/284; G01N 1/2806; G02B 21/32
(Continued)

(56) References Cited

U.S. PATENT DOCUMENTS 4,942,303 A     7/1990   Kolber et al.
5,596,408 A *   1/1997   Cummins ............ G01N 21/532
                                              356/339
(Continued)

FOREIGN PATENT DOCUMENTS

EP         2889365 A1       7/2015
WO     WO 2015/089631 A1    6/2015

OTHER PUBLICATIONS

International Search Report and Written Opinion dated Oct. 21, 2016 issued in PCT/GB2016/052485.
(Continued)

*Primary Examiner* — Md M Rahman
(74) *Attorney, Agent, or Firm* — Scully Scott Murphy & Presser, P.C.

(57) ABSTRACT

A ballast water monitoring device and a method for detecting live phytoplankton are disclosed. The device comprises a chamber for receiving a sample, at least one light source to emit light towards the sample, a light detector to receive light from the sample and generate a light signal, and a controller. The controller is configured to control the at least one light source to emit a single pulse of light, calculate the variable fluorescence [Fv] of the sample in response to the pulse of light, at time intervals less than the duration of the pulse of light, compare the calculated variable fluorescence to a predetermined reference limit, and perform an action if the calculated variable fluorescence is greater than the predetermined reference limit.

20 Claims, 19 Drawing Sheets

(51) Int. Cl.
*G01N 21/64* (2006.01)
*B63J 4/00* (2006.01)
*C02F 1/00* (2006.01)
*G01N 33/18* (2006.01)
*G01N 1/38* (2006.01)
*G01N 21/63* (2006.01)
*C02F 103/00* (2006.01)
*G01N 1/20* (2006.01)

(52) U.S. Cl.
CPC ........... *G01N 1/38* (2013.01); *G01N 21/6408* (2013.01); *G01N 21/6486* (2013.01); *G01N 33/1826* (2013.01); *C02F 2103/008* (2013.01); *C02F 2209/001* (2013.01); *C02F 2209/36* (2013.01); *C02F 2303/04* (2013.01); *G01N 2001/2064* (2013.01); *G01N 2001/386* (2013.01); *G01N 2015/0693* (2013.01); *G01N 2021/635* (2013.01); *G01N 2021/6419* (2013.01); *G01N 2021/6478* (2013.01); *G01N 2021/6482* (2013.01); *G01N 2201/064* (2013.01); *G01N 2201/0627* (2013.01); *G01N 2201/0631* (2013.01); *G01N 2201/0638* (2013.01); *G01N 2201/0696* (2013.01); *Y02A 20/206* (2018.01)

(58) Field of Classification Search
USPC .......................................................... 356/36
See application file for complete search history.

(56) References Cited

U.S. PATENT DOCUMENTS

| | | | |
|---|---|---|---|
| 6,121,053 A | 9/2000 | Kolber et al. | |
| 6,200,531 B1* | 3/2001 | Liljestrand | G01N 21/69 250/361 C |
| 2005/0073422 A1* | 4/2005 | Graff | A47L 15/4293 340/641 |
| 2005/0110998 A1 | 5/2005 | Lin et al. | |
| 2010/0068750 A1 | 3/2010 | Pogosjan et al. | |
| 2011/0117259 A1* | 5/2011 | Storek | A47J 36/14 426/509 |
| 2012/0208264 A1 | 8/2012 | Bernd et al. | |
| 2012/0308877 A1* | 12/2012 | Hirai | H01M 2/024 429/184 |
| 2012/0324986 A1 | 12/2012 | Chekalyuk | |
| 2013/0133250 A1* | 5/2013 | Chan | B01D 21/262 47/1.4 |
| 2014/0116995 A1* | 5/2014 | Berg | B23K 26/0823 219/121.6 |
| 2014/0259510 A1* | 9/2014 | Conrad | A47L 13/225 15/319 |
| 2015/0053872 A1 | 2/2015 | Kjaerulff et al. | |
| 2015/0090900 A1* | 4/2015 | Banks | G01N 21/645 250/432 R |
| 2015/0191859 A1* | 7/2015 | Webster | D06F 37/42 68/12.06 |
| 2015/0368853 A1* | 12/2015 | Kulkarni | D06F 58/28 34/446 |
| 2016/0041038 A1* | 2/2016 | Geiger | G01J 5/046 250/338.1 |
| 2016/0163177 A1* | 6/2016 | Klicpera | E03B 7/071 137/59 |
| 2016/0258870 A1* | 9/2016 | Tokhtuev | G01N 33/18 |
| 2016/0340205 A1* | 11/2016 | Murdock | C02F 1/008 |
| 2016/0348297 A1* | 12/2016 | Scheckelhoff | D06F 39/088 |

OTHER PUBLICATIONS

European Office Action dated Dec. 12, 2018 issued in EP Patent Application No. 16757050.6.

Quigg A. et al., "Phyloplankton along the coastal shelf of an oligotrophic hypersaline environment in a semi-enclosed marginal sea: Qatar (Arabian Gulf)", Continental Shelf Research, (2013), 60, pp. 1-16.

* cited by examiner

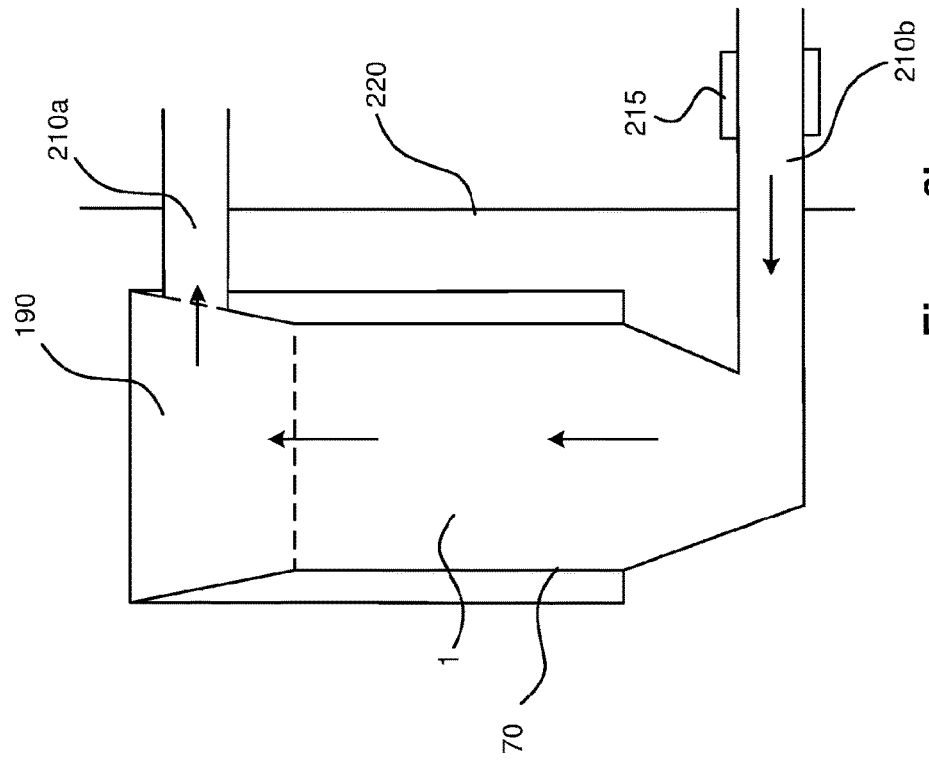
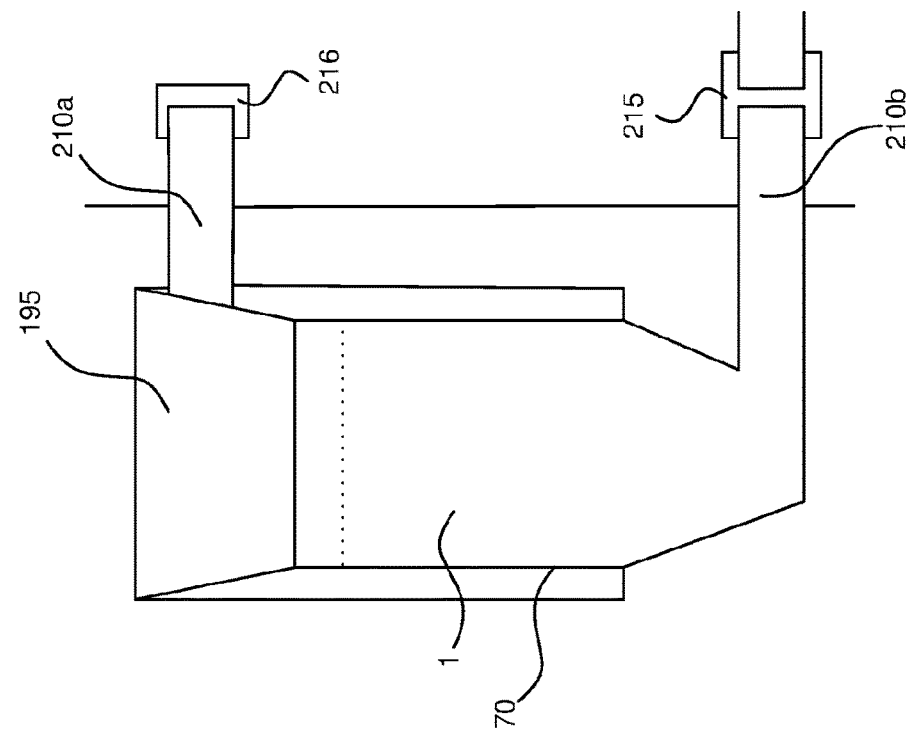
Figure 6b
Figure 6a

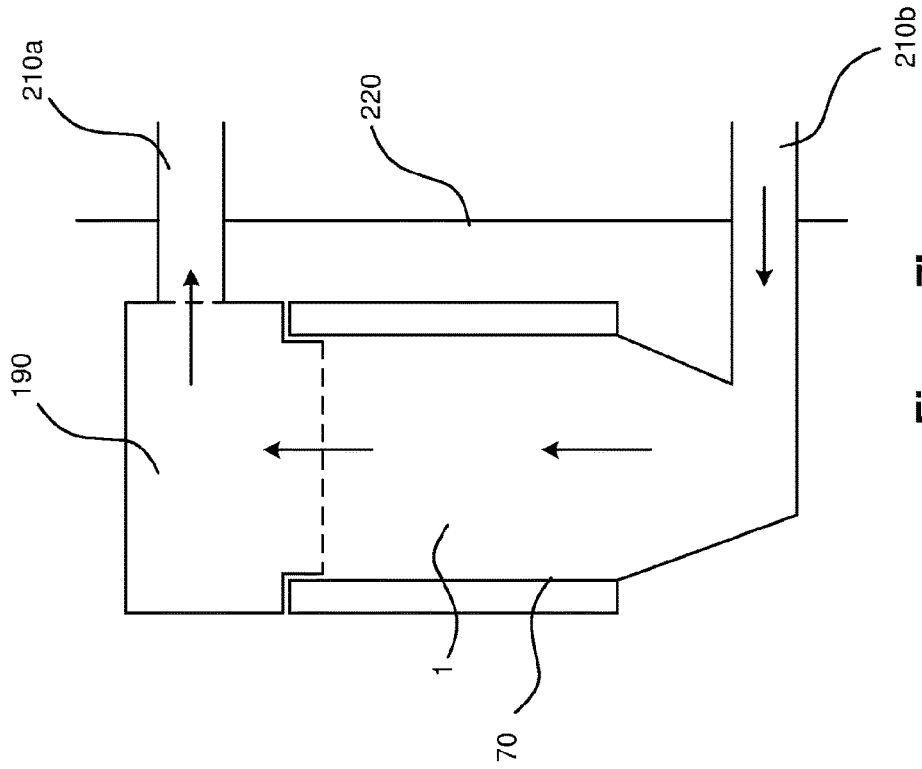
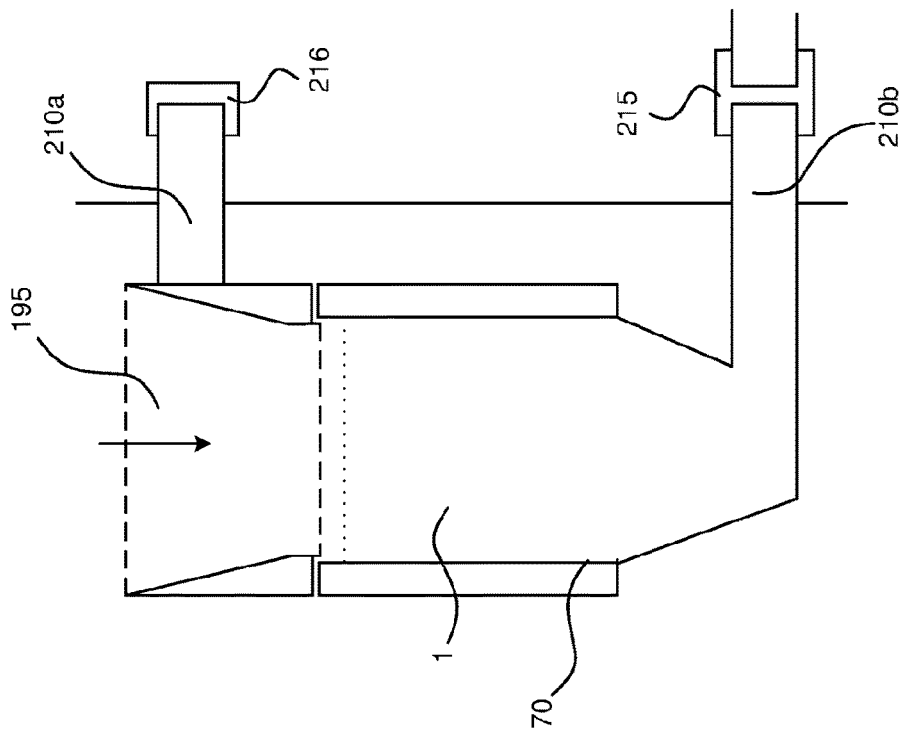
Figure 7b
Figure 7a

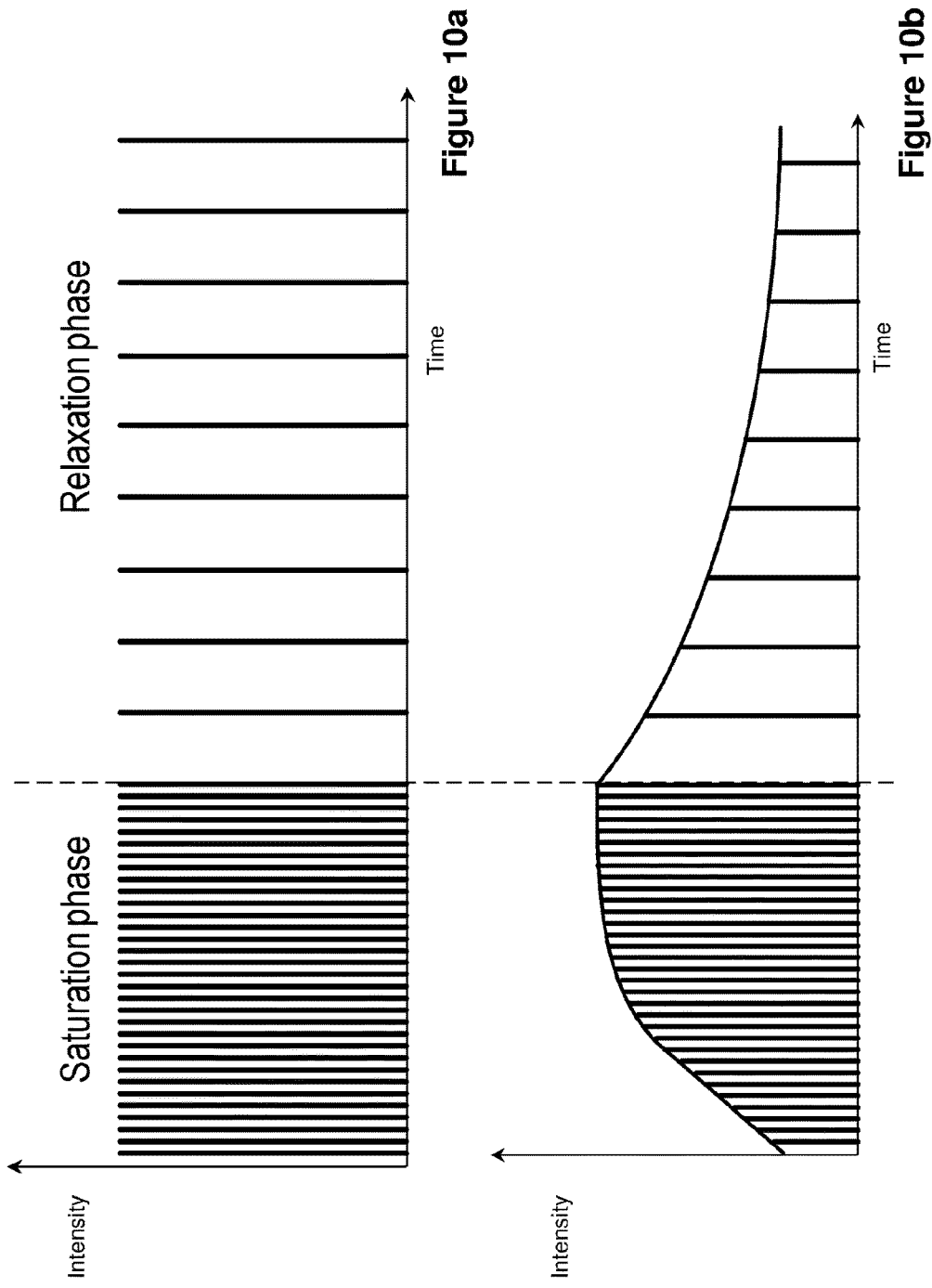

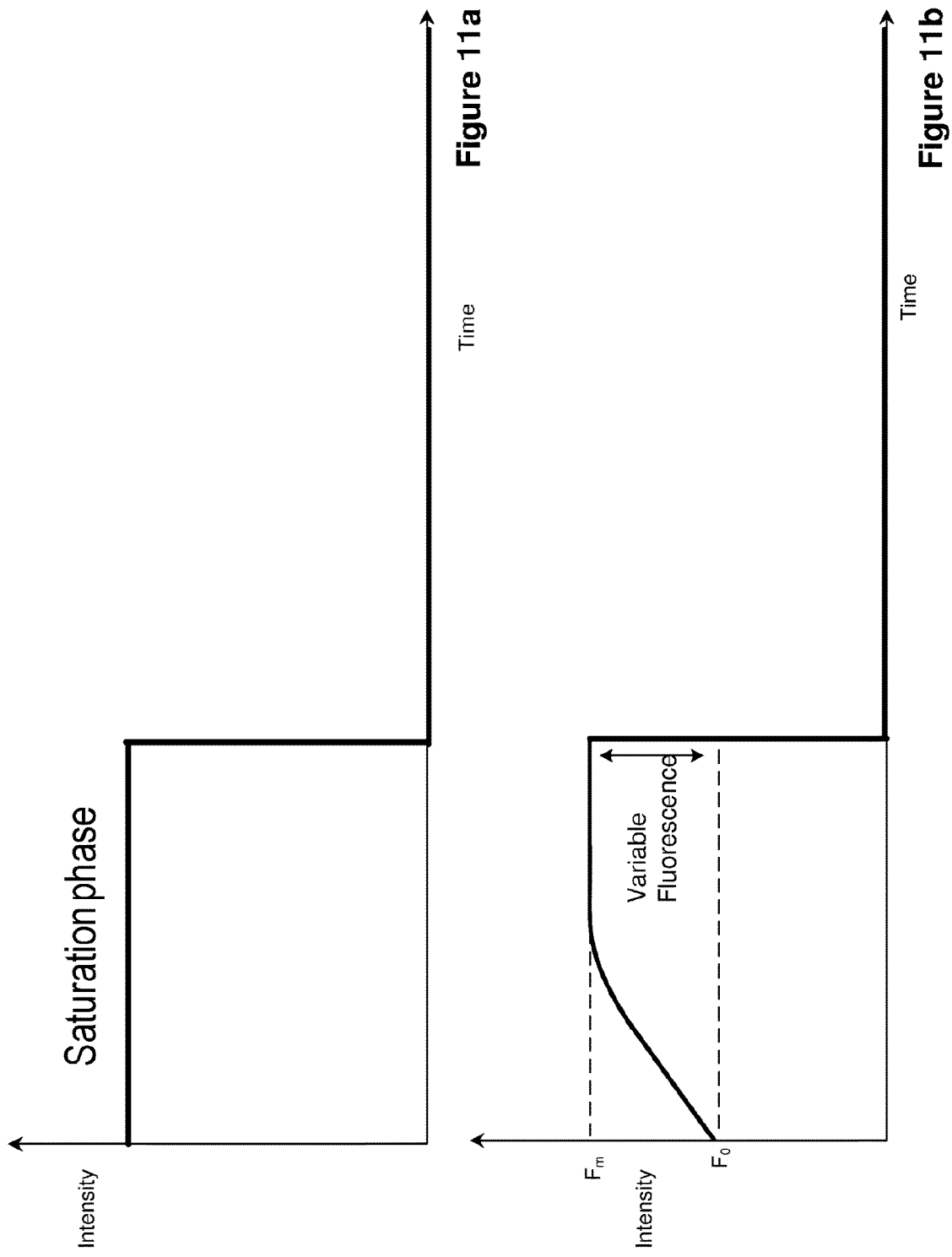

BALLAST WATER MONITORING DEVICE

FIELD

The present invention relates to ballast water monitoring devices, and in particular to the use of such devices for detecting and monitoring phytoplankton. More specifically, the invention relates to a method and ballast water monitoring device for detecting phytoplankton cells in ballast water.

BACKGROUND

The international maritime industry, with more than 70,000 merchant vessels, is responsible for transporting more than 80% of the goods traded in world markets. Accordingly, it can be viewed as a foundation of the global economy. However, commercial shipping requires the use of ballast water, which is taken up when cargo is unloaded and discharged when cargo is loaded. The ballast water can contain marine life. Accordingly, when the water is discharged it can result in the introduction of aquatic invasive species to coastal waters where they can cause enormous ecological and economic damage.

The International Maritime Organization's (IMO) International Convention for the Control and Management of Ships' Ballast Water and Sediments, adopted in 2004 but not yet ratified or entered into force, includes a discharge standard to reduce the transport and delivery of potential Aquatic Nuisance Species. Concurrently in the United States, the U.S. Coast Guard (USCG) developed and finalized ballast water discharge standards (BWDSs) that limit concentrations of living organisms that can be released with ballast water and new regulations that require ship operators to meet those limits. The USCG discharge standard, which is the same as that of the IMO, will begin to apply to ships constructed on or after Dec. 1, 2013 and for ships constructed prior to that date in 2014 or 2016, depending on ballast water capacity. To address the IMO and U.S. discharge standards, technology developers and manufacturers around the world have designed and built a variety of on-board ballast water treatment systems (BWTS) to achieve the prescribed discharge limits. To date, several dozen BWTS have been tested by independent laboratories and have received type approval certifications from various international administrations in accordance with the IMO convention. These systems include treatment processes such as: de-oxygenation, filtration, ultraviolet radiation, ozonation, and various chemical treatments, including electro-catalytic chlorination, peracetic acid, hydrogen peroxide, perchloric acid, and chlorine dioxide.

At present, there are no commercially available technologies to verify the compliance of these BWTS consistently, and in real-time. Therefore, there is a need for a rapid in situ test/device that will determine whether ballast water discharge is compliant in accordance with the IMO and USCG standards.

Aspects of the present invention aim to address one or more drawbacks inherent in prior art methods and apparatus for detecting phytoplankton cells in ballast water.

SUMMARY

According to a first aspect of the present invention, there is provided a ballast water monitoring device for detecting live phytoplankton, the device comprising:
a chamber for receiving a sample;
at least one light source to emit light towards the sample;
a light detector to receive light from the sample and generate a light signal; and
a controller configured to:
control the at least one light source to emit a single pulse of light,
calculate the variable fluorescence $[F_v]$ of the sample in response to the pulse of light, at time intervals less than the duration of the pulse of light,
compare the calculated variable fluorescence to a predetermined reference limit, and
perform an action if the calculated variable fluorescence is greater than the predetermined reference limit.

Advantageously, the ballast water monitoring device described herein has an electronic circuit design that requires less complexity than prior art devices. Additionally, the configuration eliminates the need to take background light readings which enables the number of actual readings to be increased. Therefore, the signal to noise ratio is improved over prior art devices.

The predetermined reference limit may be set according to the IMO and USCG standards. The IMO and USCG standards lay down the number of phytoplankton that may be present in ballast water if it is to be discharged. For example, the US Coast Guard Discharge Standard (10-50 μm) specifies that fewer than 10 living organisms per millilitre of ballast water may be present. The predetermined reference limit is a value of fluorescence that represents this number. The predetermined reference limit may be 0 counts per second in order for the presence of any phytoplankton to trigger the performing of the action.

The ballast water monitoring device may comprise a plurality of light sources. Each light source may be associated with a different wavelength.

The ballast water monitoring device may further comprise a means for indicating to the user that the variable fluorescence exceeds the predetermined reference limit, wherein performing an action may comprise activating the indicating means. The indicating means may be at least one of a display, an audible alarm and an indicator light.

The ballast water monitoring device may be coupled to a ballast water treatment system, and performing an action may comprise controlling the ballast water treatment system to eliminate algae. Alternatively, performing an action may comprise controlling the ballast water treatment system to eliminate live phytoplankton cells.

The pulse of light may have a duration of up to 450 μs, preferably between 50 and 400 μs, even more between 100 and 300 μs, even more preferably between 150 and 250 μs and most preferably, the pulse of light has a duration of about 200 μs.

The pulse of light may have a duration of greater than 200 μs, preferably greater than 300 μs, even more preferably between 300 μs and 500 μs, even more preferably between 350 μs and 450 μs, even more preferably between 390 μs and 410 μs and most preferably, the pulse of light has a duration of about 400 μs. Preferably, pulse of light has a pulse repetition frequency of between 10 Hz and 100 Hz, more preferably between 20 Hz and 80 Hz, even more preferably between 30 Hz and 60 Hz, and most preferably the pulse of light has a pulse repetition frequency of 40 Hz. The pulse repetition frequency is preferably less than 50 Hz.

The controller may be configured to measure the variable fluorescence by measuring the intensity of the received light at intervals of between 0.1 μs and 10 μs, preferably between 0.2 and 8 μs, even more preferably between 0.5 and 5 μs, even more preferably between 0.8 and 3 µs, and most preferably, the intensity of the received light is measured at about 1 µs intervals.

The at least one light source may be configured to emit a pulse of light comprising one or more of Royal Blue light, Blue light, Red light or Green light. When there are a plurality of light sources, the plurality of light sources may be configured to emit a pulse of light comprising any combination of two or more of Royal Blue light, Blue light, Red light or Green light simultaneously. It would be understood by the skilled person that Royal Blue light has a central wavelength of about 450 nm, and Blue light has a central wavelength of about 470 nm. It would be understood by the skilled person that Green light has a wavelength of between 495 nm and 570 nm, and Red light has a wavelength of between 620 nm and 720 nm. Preferably, the at least one light source may be configured to emit a pulse of light having a wavelength of at least one of about 450 nm, 470 nm, 530 nm, and 624 nm. Even more preferably, wherein when there are a plurality of light sources, the plurality of light sources may be configured to emit a pulse of light having wavelengths of at least two of about 450 nm, 470 nm, 530 nm, and 624 nm simultaneously.

The chamber may comprise an inlet and an outlet, through which water can continuously flow. The chamber may comprise a removable blocking member for blocking the inlet or the outlet to allow a discrete sample to be measured. The chamber may comprise at least one valve arranged in the inlet or the outlet to block the inlet or the outlet to allow a discrete sample to be measured.

The ballast water monitoring device may further comprise a plurality of lenses configured to generate a uniform light field directed into the chamber. At least one of the plurality of lenses may be an achromatic doublet lens to direct light of multiple wavelengths into the chamber. Alternatively, the light of multiple wavelengths may be directed into the chamber by arranging the plurality of light sources on a curved surface. The plurality of lenses may comprise an array of plano-convex lenses positioned directly in front of the plurality of light sources. Additionally, the plurality of lenses may comprise a shortpass filter placed in front of the array of plano-convex lenses. Preferably, the shortpass filter is a shortpass interference filter.

The controller may be configured to estimate a minimal fluorescence [$F_0$] of the sample using regression analysis of a first part of the generated light signal, estimate a maximal fluorescence [$F_m$] of the sample using regression analysis of a second part of the generated light signal, and subtract $F_0$ from $F_m$ to provide $F_v$.

The controller may be configured to repeat the steps of:
controlling the at least one light source to emit a single pulse of light, and
calculating the variable fluorescence [$F_v$] of the sample in response to the pulse of light, at time intervals less than the duration of the pulse of light, and may be further configured to:
average the calculated variable fluorescence over the number of repetitions; and
perform the action if the average calculated variable fluorescence is greater than the predetermined reference limit.

Advantageously, averaging the variable fluorescence over a number of cycles performed on the same sample improves the signal to noise ratio.

The ballast water monitoring device may further comprise a stirrer for stirring the sample. The blocking member may comprise the stirrer. Alternatively, the stirrer may be arranged to pass through a side wall of the chamber.

According to a second aspect of the present invention, there is provided a system comprising:
a ballast water treatment system; and
the ballast water monitoring device according to the first aspect of the invention,
wherein the ballast water monitoring device controls the ballast water treatment system to activate a means for eliminating live phytoplankton cells.

According to a third aspect of the present invention, there is provided a method of determining whether live phytoplankton are present in a sample, the method comprising:
generating a pulse of light and directing it towards the sample;
receiving light from the sample in response to receiving the pulse of light, and generating a light signal;
calculating the variable fluorescence [$F_v$] of the sample in response to receiving the pulse of light at time intervals less than the duration of the pulse of light;
comparing the calculated variable fluorescence to a predetermined reference limit; and
performing an action if the calculated variable fluorescence exceeds the predetermined reference limit.

Generating the pulse of light may comprise activating a plurality of light sources, each being associated with a different wavelength.

Performing the action may comprise indicating that the variable fluorescence exceeds the predetermined reference limit. Performing the action may comprise controlling a means for exterminating algae. Alternatively, performing the action may comprise controlling a means for exterminating live phytoplankton cells.

The pulse of light may have a duration of up to 450 µs, preferably the pulse of light has a duration of between 50 and 400 µs, even more preferably the pulse of light has a duration of between 100 and 300 µs, even more preferably the pulse of light has a duration of between 150 and 250 µs and most preferably, the pulse of light has a duration of 200 µs. Alternatively, the pulse of light may have a duration of greater than 200 µs, more preferably greater than 300 µs, even more preferably between 300 µs and 500 µs, even more preferably between 350 µs and 450 µs, even more preferably between 390 µs and 410 µs and most preferably, the pulse of light has a duration of about 400 µs. Preferably, pulse of light has a pulse repetition frequency of between 10 Hz and 100 Hz, more preferably between 20 Hz and 80 Hz, and most preferably between 30 Hz and 60 Hz. The pulse repetition frequency is preferably less than 50 Hz.

The method may comprise measuring the variable fluorescence by measuring the intensity of the received light at intervals of between 0.1 and 10 µs, preferably between 0.2 and 8 µs, even more preferably between 0.5 and 5 µs, even more preferably between 0.8 and 3 µs, and most preferably, the intensity of the received light is measured at 1 µs intervals.

The pulse of light may comprise any one of Royal Blue light, Blue light, Red light or Green light. The pulse of light may comprise any combination of two or more of Royal Blue light, Blue light, Red light or Green light. It would be understood by the skilled person that Royal Blue light has a central wavelength of about 450 nm, and Blue light has a central wavelength of about 470 nm. It would be understood by the skilled person that Green light has a wavelength of between 495 nm and 570 nm, and Red light has a wavelength of between 620 nm and 720 nm. Preferably, the pulse of light is configured to have a wavelength of at least one of about 450 nm, 470 nm, 530 nm, and 624 nm. Even more preferably, wherein when a plurality of light sources are activated, the pulse of light is configured to have wavelengths of at least two of about 450 nm, 470 nm, 530 nm, and 624 nm.

The method may comprise generating a uniform light field and directing it into a chamber in which the sample is contained.

The method may comprise estimating $F_0$ of the sample using regression analysis of a first part of the generated light signal, estimating $F_m$ of the sample using regression analysis of a second part of the generated light signal, and subtracting $F_0$ and $F_m$ to provide $F_v$. The regression analysis may be linear regression.

The method may further comprise repeating the steps of:
controlling the at least one light source to emit a single pulse of light, and
calculating the variable fluorescence [$F_v$] of the sample in response to the pulse of light, at time intervals less than the duration of the pulse of light, and may further comprise:
averaging the calculated variable fluorescence over the number of repetitions, and
performing the action if the average calculated variable fluorescence is greater than the predetermined reference limit.

The method may further comprise stirring the sample before repeating the step of controlling the at least one light source to emit a single pulse of light.

According to a fourth aspect of the present invention, there is provided a ballast water monitoring device for detecting live phytoplankton, the device comprising:
a chamber for receiving a sample; at least one light source to emit light towards the sample;
a light detector to receive light from the sample; and
a controller configured to:
control the at least one light source to emit a single pulse of light,
calculate the variable fluorescence [$F_v$] of the sample in response to the pulse of light, at time intervals less than the duration of the pulse of light,
compare the calculated variable fluorescence to a predetermined reference limit, and
perform an action if the calculated variable fluorescence is greater than the predetermined reference limit.

The controller may be configured to estimate a minimal fluorescence [$F_0$] of the sample using linear regression, and subtract that value from the maximal fluorescence [$F_m$] to provide $F_v$.

The at least one light source may be configured to emit a pulse of light comprising one or more of Royal Blue light, Blue light, Red light or Green light. When there are a plurality of light sources, the plurality of light sources may be configured to emit a pulse of light comprising any combination of two or more of Royal Blue light, Blue light, Red light or Green light simultaneously. It would be understood by the skilled person that Royal Blue light has a wavelength of about 450 nm, and Blue light has a wavelength of about 470 nm. It would be understood by the skilled person that Green light has a wavelength of between 495 nm and 570 nm, and Red light has a wavelength of between 620 nm and 720 nm. Preferably, the at least one light source may be configured to emit a pulse of light having a wavelength of at least one of about 450 nm, 470 nm, 530 nm, and 620 nm. Even more preferably, wherein when there are a plurality of light sources, the plurality of light sources may be configured to emit a pulse of light having wavelengths of at least two of about 450 nm, 470 nm, 530 nm, and 620 nm simultaneously.

The controller may be configured to measure the variable fluorescence by measuring the intensity of the received light at intervals of between 0.1 µs and 10 µs, preferably between 0.2 and 8 µs, even more preferably between 0.5 and 5 µs, even more preferably between 0.8 and 3 µs, and most preferably, the intensity of the received light is measured at about 1 µs intervals.

According to a fifth aspect of the present invention, there is provided a system comprising:
a ballast water treatment system; and
the ballast water monitoring device according to the fourth aspect of the invention,
wherein the ballast water monitoring device controls the ballast water treatment system to activate a means for eliminating algae.

According to a sixth aspect of the present invention, there is provided a method of determining whether live phytoplankton are present in a sample, the method comprising:
generating a pulse of light and directing it towards the sample;
calculating the variable fluorescence [$F_v$] of the sample in response to receiving the pulse of light at time intervals less than the duration of the pulse of light;
comparing the calculated variable fluorescence to a predetermined reference limit; and
performing an action if the calculated variable fluorescence exceeds the predetermined reference limit.

The pulse of light may comprise any one of Royal Blue light, Blue light, Red light or Green light. The pulse of light may comprise any combination of two or more of Royal Blue light, Blue light, Red light or Green light. It would be understood by the skilled person that Royal Blue light has a wavelength of about 450 nm, and Blue light has a wavelength of about 470 nm. It would be understood by the skilled person that Green light has a wavelength of between 495 nm and 570 nm, and Red light has a wavelength of between 620 nm and 720 nm. Preferably, the pulse of light is configured to have a wavelength of at least one of about 450 nm, 470 nm, 530 nm, and 620 nm. Even more preferably, wherein when a plurality of light sources are activated, the pulse of light is configured to have wavelengths of at least two of about 450 nm, 470 nm, 530 nm, and 620 nm.

The method may comprise measuring the variable fluorescence by measuring the intensity of the received light at intervals of between 0.1 and 10 µs, preferably between 0.2 and 8 µs, even more preferably between 0.5 and 5 µs, even more preferably between 0.8 and 3 µs, and most preferably, the intensity of the received light is measured at 1 µs intervals.

The method may comprise estimating a minimal fluorescence [$F_0$] of the sample using regression analysis, and subtracting that value from the maximal fluorescence [$F_m$] to provide $F_v$.

All features described herein (including any accompanying claims, abstract and drawings), and/or all of the steps of any method or process so disclosed, may be combined with any of the above aspects in any combination, except combinations where at least some of such features and/or steps are mutually exclusive.

BRIEF DESCRIPTION OF THE FIGURES

Embodiments of the present invention will now be described, by way of example only, with reference to the accompanying drawings, in which:

FIG. 6a and FIG. 6b show cross sections of the ballast water monitoring device of FIG. 5, operating in discrete-sampling mode and flow-through mode respectively;

FIG. 7a and FIG. 7b show cross sections of the ballast water monitoring device of FIG. 5, operating in discrete-sampling mode and flow-through mode respectively;

FIGS. 10a and 10b show an example of an excitation profile and fluorescence response of chlorophyll-a according to a prior art device;

FIGS. 11a and 11b show an example of an excitation profile and fluorescence response of chlorophyll-a according to an embodiment of the device of the invention;

DETAILED DESCRIPTION

Figure 1:
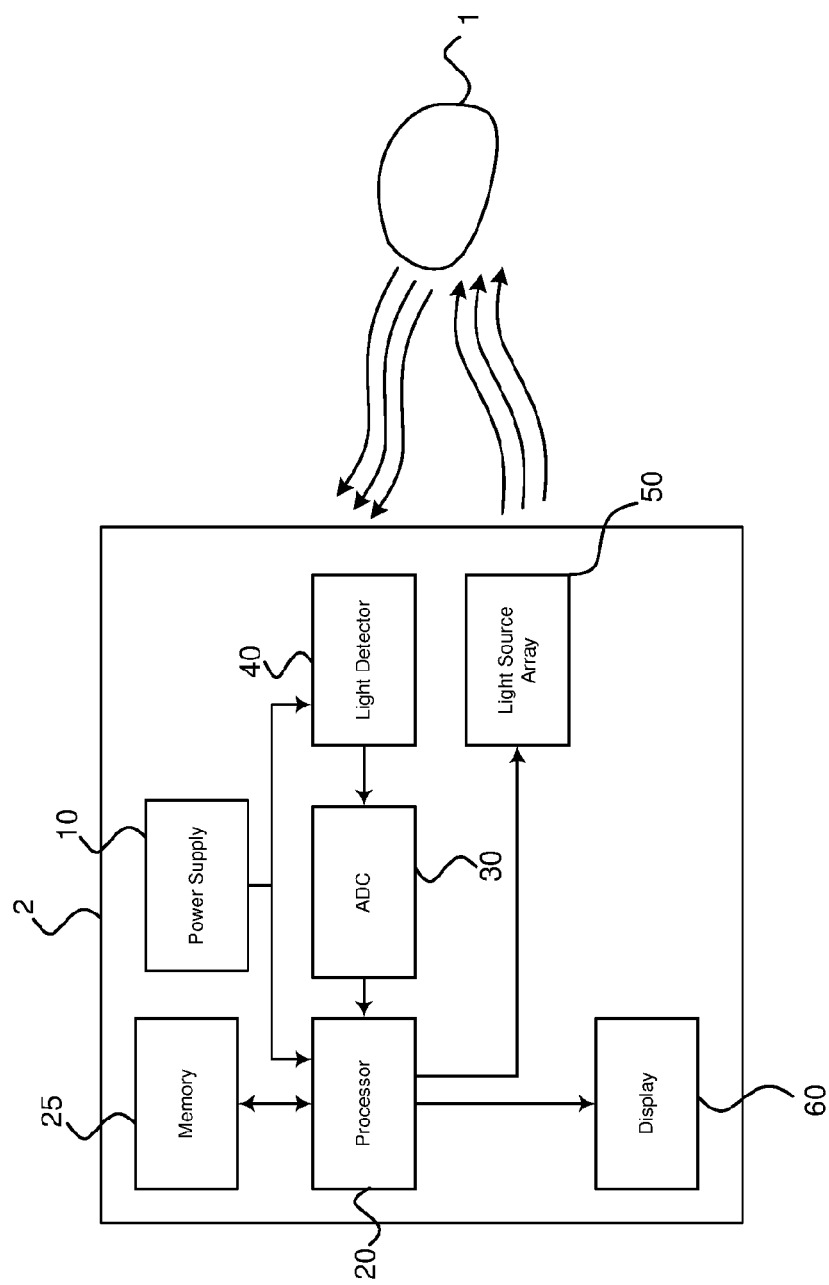
FIG. 1 shows a system diagram of a ballast water monitoring device according to an embodiment of the present invention.

With reference to FIG. 1, a ballast water monitoring device 2 is shown that includes a light source array 50 and a light detector 40 for measuring the response of a sample 1 to applied optical radiation. For example, the sample 1 is ballast water in the hull of a water-borne vessel, such as a yacht, cargo ship, or submarine, which contains unidentified phytoplankton. The ballast water monitoring device 2 is configured to determine the presence of phytoplankton in the 10 to 50 μm range. The phytoplankton are suspended in the water, and fluoresce when exposed to light of certain wavelengths. Thus, the device 2 can be used to differentiate between different species of phytoplankton present in ballast water of a vessel transiting from region A to region B, and monitor algal populations to assist safeguarding against the unwanted to spread of these invasive species to coastal waters where they can cause ecological and economic damage.

The ballast water monitoring device 2 includes a power supply 10. The power supply 10 may be, for example, a removable 15 V lithium ion battery operating at 2.2 Ah. Where the power supply 10 is a battery, an integral charger may be provided so that the battery pack need not be removed from the enclosure in order to be charged. Alternatively, the power supply 10 may be an adapter for coupling the ballast water monitoring device 2 to an external power supply. External power is provided from an external 15 V universal input (110-240 VAC) power supply.

The power supply 10 supplies power to the light detector 40. The light detector 40 in an exemplary embodiment is a photomultiplier tube (herein referred to as a PMT). The PMT 40 detects light that is emitted from the sample 1, and applies a gain to the signal so that it can be measured. The PMT 40 may be, for example, a Hamamatsu R9880U-20. Alternatively, the light detector 40 may comprise a photodiode, an avalanche photodiode, or a multi-pixel photon counter.

The light detector 40 is coupled to an analogue to digital converter (ADC) 30. The ADC converts the signal detected by the light detector 40 into a digital signal that can be interpreted and processed by a processor 20. The processor 20 is configured to use the signal received from the ADC 30 to calculate the variable fluorescence ($F_v$) of the sample 1. Any measurable variable fluorescence indicates that the sample 1 is likely to be in breach of the IMO D2 Standard (10-50 μm) and the US Coast Guard Discharge Standard (10-50 μm).

Although the light detector 40 is shown in FIG. 1 as being separate from the processor 20, other configurations are possible that provide further advantageous effects. For example, in some embodiments, the processor 20 comprises a detector board which includes the PMT 40, a pre-amplifier, PMT high voltage supply and control for the high voltage supply. Ambient overload protection circuitry is incorporated into the detector board. A photodiode is further included for built-in testing and diagnostics.

The processor 20 in an exemplary embodiment is based on the XilinX ZynQ 7000 System on Chip (SoC). The Zynq7 IC features a sophisticated processing and programmable logic core. The processing system (PS) integrates two ARM® Cortex™-A9 MPCore™ application processors, AMBA® interconnect, internal memories, external memory interfaces, and peripherals including USB, Ethernet, SPI, SD/SDIO, I2C, CAN, UART, and GPIO. The PS runs independently of the programmable logic and boots at power-up or reset. The core processor 20 runs a bootloader (u-boot) and embedded Linux operating system from a binary image stored on the SD card. An on-board 2 Mb SDRAM (e.g. H5TQ2G63DFR-RDC) is used by the Linux as a ram drive and system memory.

The ballast water monitoring device 2 further includes a display 60. The display 60 may be a resistive touch screen display, such as the eDIPTFT32-A. The processor 20 is configured to control the display 60 using a display driver stored in the memory 25. Alternatively, or in addition to the display 60, the ballast water monitoring device 2 may comprise an audible alarm, or an LED indicator.

In some embodiments, which do not require the ballast water monitoring device 2 to have a display 60, the ballast water monitoring device 2 comprises at least one interface (in other words, at least one data port) to couple the ballast water monitoring device 2 to a computing device such as a tablet or PC, so that the computing device can be used to program the ballast water monitoring device 2 and/or display primary data transferred to the computing device from the ballast water monitoring device 2 via the interface. The at least one interface may be a USB interface, a Bluetooth interface an Ethernet interface, or a combination thereof. The skilled person would appreciate that these are exemplary examples of interfaces, and the ballast water monitoring device 2 may include any suitable wired or wireless means for coupling to an external computing device. A remote control graphical user interface (GUI) operating on the computer provides more advanced control and operation of the instrument via the interface. The GUI also allows the instrument configuration and code to be maintained. The ballast water monitoring device 2 having the interface is not limited to embodiments not having a display 60.

The power supply 10 supplies power to the processor 20. The processor 20 is configured to control the light source array 50 using a light source array driver stored in a memory 25. Alternatively, the light source array 50 may be controlled by an LED-on-chip module on the processor 20. The function of the light source array driver is to provide highly reproducible current pulses, of software-controllable amplitude and duration.

Figure 2:
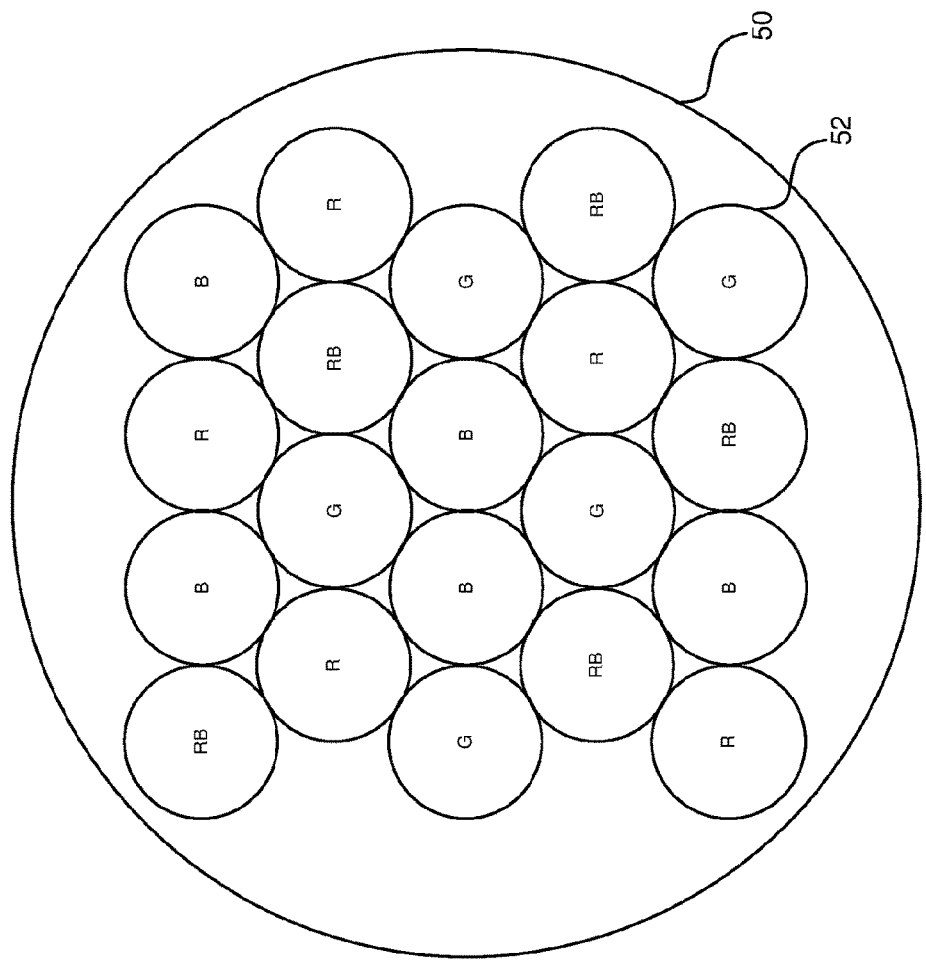
FIG. 2 shows a light source array according to an embodiment of the device.

The light source array 50 according to an exemplary embodiment will now be described with reference to FIG. 2. The light source array 50 is driven to generate an excitation pulse lasting between 200 and 500 μs at a pulse repetition frequency (PRF) of between 10 Hz and 50 Hz. Preferably the excitation pulse is configured to last 400 μs and has a PRF of 40 Hz, while measurements are taken every 1 μs that the pulse is on. This is repeated multiple times. Using a continuous pulse provides a number of advantages, for example, the electronic circuit design requires less complexity, and it eliminates the need to take background light readings which enables the number of actual readings to be increased. Therefore, the signal to noise ratio is improved. The light source array 50 may be a single light source. Alternatively, the light source array 50 may comprise a plurality of light sources. The excitation pulse generated by the embodiment shown in FIG. 2 is a composite pulse of light having multiple wavelengths. The multiple wavelength excitation is achieved with an array of LEDs 52 of different colours, covering the spectral range between 400 and 640 nm. The drive current for each LED 52 is chosen using the light source driver to ensure that single turnover saturation is achieved within the duration of the excitation pulse. An LED rail voltage of +22 V is required to drive the LEDs 52. The light sources may be mounted on a printed circuit board (PCB).

In some embodiments, the light source array 50 is an array of twenty LEDs 52, arranged in four banks of five connected in series. As shown in FIG. 2, the light source array 50 generates light using Royal Blue, Blue, Green, and Red LEDs.

Respectively, the different LEDS 52 preferably emit light having wavelengths of about 450 nm, 470 nm, 530 nm, and 624 nm, although the skilled person would recognise that Royal Blue light has a central wavelength of about 450 nm, Blue light has a central wavelength of about 470 nm, Red light has a wavelength of between 620 nm and 720 nm, and Green light has a wavelength of between 495 nm and 570 nm. Different species of phytoplankton react more strongly to different wavelengths of radiation. Examples are shown in FIGS. 12a to 12f. In other words, by using multiple wavelengths, the ballast water monitoring device 2 is able to detect a wide range of species. By exciting all major pigment groups found in phytoplankton, it can be determined to a high probability that a negative result is a true indicator that the number of living phytoplankton cells present in the sample is less than a threshold.

In alternative embodiments, the Green and Red LEDs can be replaced with Royal Blue and Blue LEDs. This provides the advantage of an increase in the intensity of the illumination at the Royal Blue and Blue frequencies, which decreases the response time of the phytoplankton. In further embodiments, the LEDs 52 in the array all emit the same colour of light to further increase the intensity of illumination at a particular wavelength.

In alternative embodiments, the light source array 50 comprises a plurality of lasers, each emitting light at a different spectral wavelength. The plurality of lasers are configured to emit light covering the spectral range between 400 and 640 nm. In an exemplary embodiment, the plurality of lasers emit light at 450 nm, 470 nm, 530 nm and 634 nm respectively. In further embodiments, the light source array 50 comprises a single laser configurable to emit light at a plurality wavelengths. In an exemplary embodiment, the single laser is configurable to emit light at 450 nm, 470 nm, 530 nm, and 634 nm.

The light source array 50 is configured to generate a photon flux density of 20,000 micromoles of photons per metre squared per second, which is several times the photon flux density of sunlight, within the wavelength range.

Prior art devices use the Fast Repetition Rate (FRR) technique in measuring the fluorescence of the sample 1, as explained later with reference to FIGS. 10a and 10b. However, according to embodiments of the present invention, the processor 20 is configured to apply an alternative to the FRR technique in measuring the fluorescence of the sample 1. More specifically, according to an exemplary embodiment, the processor 20 uses a single turnover method to measure any variable fluorescence ($F_v$) present in a water sample 1 contained in an integral chamber 70 (described later with reference to FIG. 3). $F_v$ is calculated by measuring the maximal fluorescence ($F_m$) of the sample 1, and subtracting the minimal fluorescence ($F_0$) from $F_m$. $F_0$ is estimated using linear regression to extrapolate a sequence of 10-20 μs back to time t=0. The skilled person would appreciate that other regression techniques may be used, such as polynomial regression or quantile regression. The technique for measuring fluorescence according to the present invention is shown in more detail in FIGS. 11a and 11b.

The water sample 1 will be in the dark and so phase sensitive detection is not required. Up to 800 measurements of incoming radiation are taken at 1 μs intervals before, during and after the pulse. The data is processed in real time with the results presented to the user on the display 60.

If the calculated value of $F_v$ is greater than a predetermined limit, then the user is warned that the amount of phytoplankton in the ballast water may exceed legislative values. In an exemplary embodiment, the user is warned by a message on the display 60. Alternatively, the user may be warned with an audible alarm, or with an indicator light. $F_v$ has been selected to indicate compliance with the IMO and USCG standards.

In some embodiments, a number of cycles, or interrogations, are performed on the same sample 1. In other words, a plurality of pulses are used to illuminate the sample 1 and the value of $F_v$ is calculated for each pulse. The values of $F_v$ are then averaged over the number of cycles. The average calculated value of $F_v$ is then compared against the predetermined limit. The sample 1 may be stirred between each cycle. Advantageously, this improves the signal to noise ratio. This will be explained in more detail later.

Where the ballast water monitoring device 2 is integrated into a closed system, or, in other words, is integrated into the ballast tank of a vessel, the processor 20 may be configured to prevent ballast water being emptied when $F_v$ is greater than the predetermined limit. Alternatively, or additionally, the processor 20 may be configured to activate a means for killing the live phytoplankton, which can include treatment processes such as: de-oxygenation, filtration, ultraviolet radiation, ozonation, and various chemical treatments, including electro-catalytic chlorination, peracetic acid, hydrogen peroxide, perchloric acid, and chlorine dioxide. This prevents the ballast water, containing living phytoplankton, from being output into the sea. By integrating the ballast water monitoring device 2 into a closed system, the vessel is able to store fewer chemicals, and expend less energy, as the ballast water is only treated when the ballast water monitoring device 2 determines it is necessary to do so.

An external pump is used to deliver the sample 1 to the chamber 70. For example, a pump in the closed system described above may pump the sample 1 into the chamber 70. In other embodiments, the ballast water monitoring device 2 further comprises a pump for delivering the water sample 1 to the chamber 70.

The ballast water monitoring device 2 is arranged to operate in near-real time. Additionally, the processor 20 is configurable to either integrate data continuously, providing a live update of conformance during ballast water discharge, or process data from discrete samples and, if required to remove ambiguity, filtered sub-samples.

Figure 3:
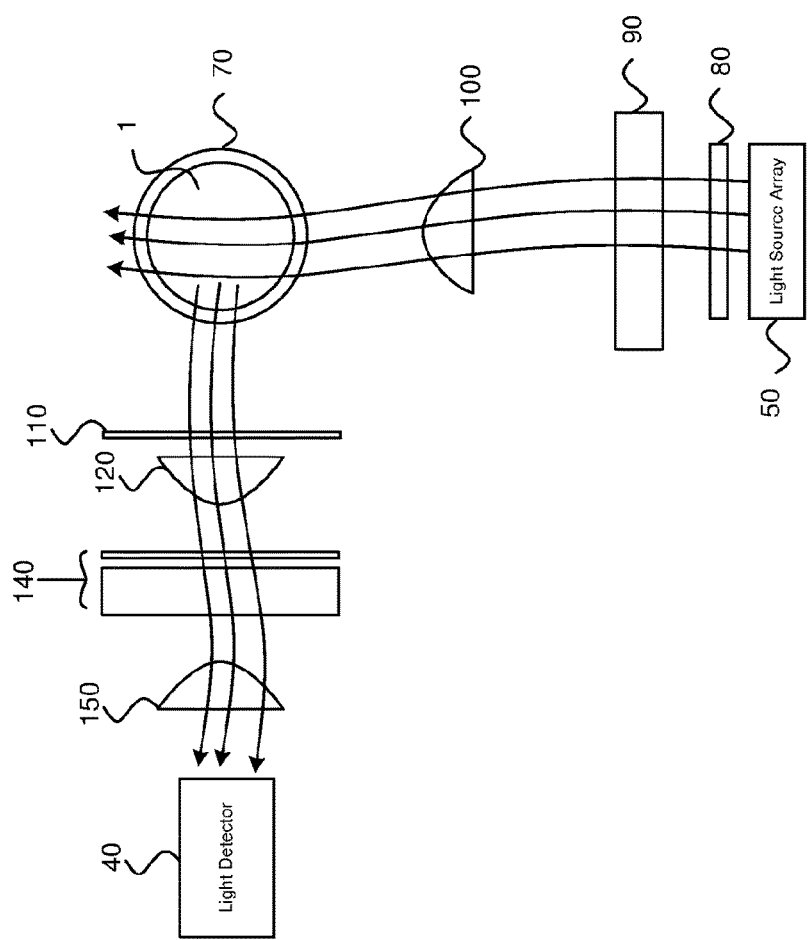
FIG. 3 shows an optical arrangement of the ballast water monitoring device shown in FIG. 1.

An optical arrangement for measuring the fluorescence of a sample 1 is shown in FIG. 3. The fluorometer is arranged with a right-angled excitation/emission geometry.

The optical design of the ballast water monitoring device 2 is optimised to direct the greatest amount of the light output from the light source array 50 into a chamber 70. The chamber 70 is made of any suitable non-luminescent material. The chamber 70 may be made of fused-silica, for example. Alternatively, the chamber 70 may be made of Pyrex, acrylic, or glass. The chamber 70 for holding the sample 1 is part of the ballast water monitoring device 2, despite not being shown in the system diagram of FIG. 1. The chamber 70 is open-ended, to allow continuous flow-through.

To achieve this optimisation, an array of plano-convex lenses 80 is positioned directly in front of the light source array 50 to roughly collimate the output from each light source 52 in the light source array 50. A shortpass interference filter 90 is placed in front of the array of plano-convex lenses to block any longer wavelength emission from the light sources 52 that could be picked-up at the fluorescence detection wavelengths. In other embodiments, a shortpass filter, such as a shortpass coloured glass filter, is used in place of the shortpass interference filter 90. The light source array 50 is placed in the back focal plane of an achromatic doublet lens 100, which effectively produces an image of each light source 52 die at infinity. However, this also has the effect of converging the output from each light source 52 at the front focal plane of the achromatic doublet to produce a uniform distribution of light intensity. This convergence point is positioned at the centre of the sample chamber 70. The use of an achromatic doublet lens 100 ensures that the same focal point is achieved for each of the four excitation wavelengths. The uniform light distribution is further improved by using the LED colour distribution shown in FIG. 2.

Figure 4:
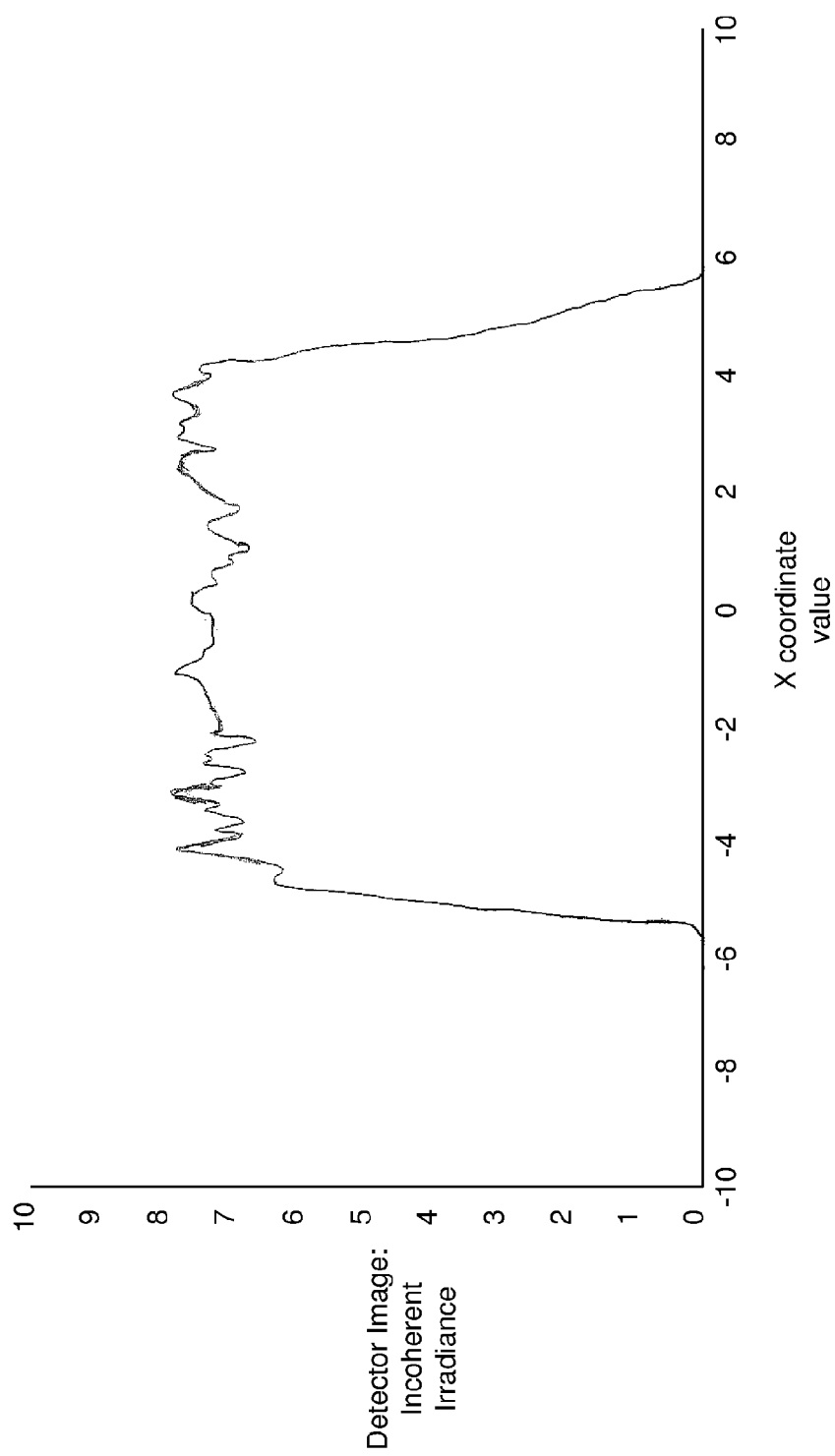
FIG. 4 shows a cross section of an illumination field generated by the optical arrangement shown in FIG. 3.

The uniform distribution of light is shown in FIG. 4. The graph in this Figure shows light intensity plotted against position. In other words, the Figure shows light intensity being roughly the same across the width of the chamber 70. A uniform light field directed into the chamber 70 provides the advantage of reducing the number of artefacts in the measurement response. If all phytoplankton cells within the sample 1 are not subjected to the same light field, then they will saturate over different timescales and the signal response will be distorted. The detection optics are designed to image the central uniform illumination area onto the light detector 40. This emission path will now be described in more detail by referring back to FIG. 3. The combination of the light source array 50 and array of plano-convex lenses 80 provides homogeneous illumination to the sample 1.

The emission path is a condenser arrangement for collimating the fluorescence emitted from the sample 1. The emission path comprises a first plano-convex lens 120 and a second plano-convex lens 150 sandwiching an optical (emission) filter 140. The optical filter 140 may be chosen to remove wavelengths of light from the collimated light that are not within the spectral range of fluorescence emitted by PSII within live phytoplankton cells. For example, the optical filter 140 is a bandpass interference filter with a peak at 682 nm and a half band width of 30 nm. However, the optical filter 140 may also be a suitable longpass interference filter, longpass absorptive filter or dichroic filter. Preferably, the optical filter 140 is arranged to transmit chlorophyll fluorescence at 683 nm. The focal length of these lenses is selected to ensure that the area of uniform illumination generated across the sample 1 is imaged onto the active area of the light detector 40.

Apertures (not shown) are arranged throughout the emission and excitation optical paths to minimise interference from scattered light.

Figure 5:
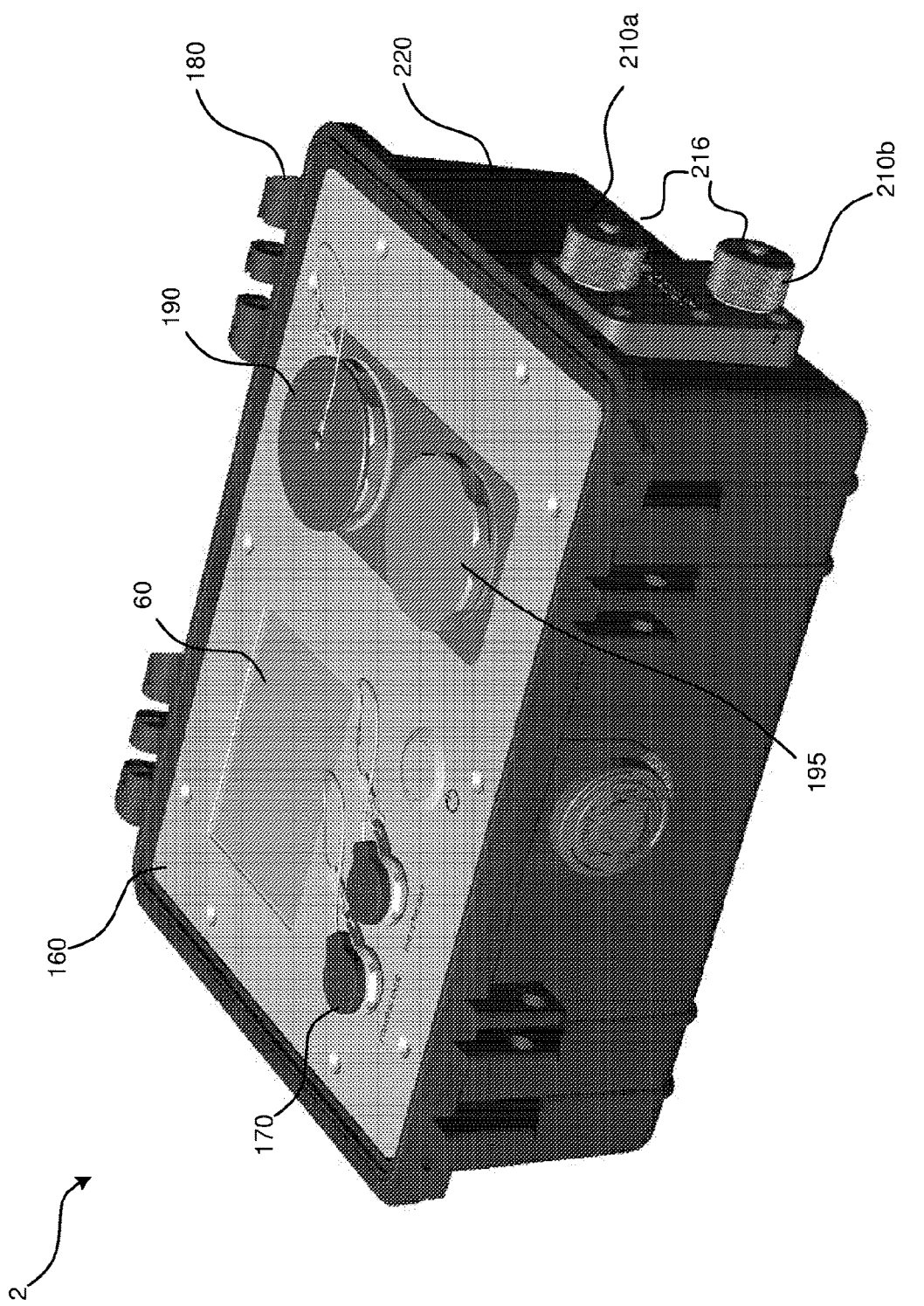
FIG. 5 shows an external perspective view of one embodiment of the ballast water monitoring device.

FIG. 5 shows a perspective view of the ballast water monitoring device 2 according an embodiment. The ballast water monitoring device 2 comprises an outer case 220. The outer case 220 includes a hinge 180 for coupling the outer case 220 to a lid (not shown). The outer case 220 further comprises data ports 170 (or interfaces) for connecting the water ballast monitoring device 2 to another device, such as a computing device, by wired connection such as by USB and/or Ethernet cable. In some embodiments, wireless communication between the ballast water monitoring device 2 and a computing device is also possible through Bluetooth communication or any other known wireless communication means. The case 220 further comprises a charger socket for connecting the water ballast monitoring device 2 to an external power supply, such as the electricity supply of a ship. Waterproof bulkhead connectors are used for these connections.

The ballast water monitoring device 2 weighs less than 4 kg. The size of the ballast water monitoring device 2 (excluding connectors) does not exceed 340×220×100 mm.

The ballast water monitoring device 2 comprises a top plate 160, which incorporates the display 60 and external electrical connections 170. An optics block is mounted underneath the top plate 160 to support the chamber 70, associated optics and fluid paths and the main electronics boards, namely: the processor 20, light detector 40 and light source array 50 driver boards. The power supply 10 is mounted separately to the top plate 160. A metal enclosure (not shown) provides EMC screening for the fluorometer.

External fluid connectors 210a, 210b are located at the side of the case 220. The external fluid connectors 210a, 210b are in fluidic communication with the inside of the chamber 70. The two fluid connectors 210a, 210b are ⅜" BSP ports that provide standard threaded connectors. In some embodiments, ½" BSP connections are used.

The ballast water monitoring device 2 is configurable to operate in both discrete-sampling mode and in flow-through mode. In some embodiments, switching between these two modes is achieved by swapping blocking members 190, 195. Here, the blocking members 190, 195 are threaded inserts, but in other embodiments the blocking members 190, 195 may be retained by friction or a clip, rather than a screw thread. In the example shown in FIG. 5, the ballast water monitoring device 2 is configured to operate in discrete-sample mode. The blocking member 195 inserted approximately opposite the fluid connectors 210a, 210b determines the mode of operation. The other blocking member 190 is in a stored position, and does not perform a function until moved to the position approximately opposite the fluid connectors 210a, 210b. In some embodiments, taps or valves attached to either or both the upper fluid connector 210a or lower fluid connector 210b act as blocking members to allow a sample 1 to enter or leave the chamber 70. No tools are required for routine operations, including switching between flow-through and discrete-sample modes.

Flow-through and discrete-sample modes will now be described in more detail with reference to FIGS. 6a and 6b. In discrete-sample mode (FIG. 6a), a blocking member 195 in the form of a solid funnel insert is provided to block the upper fluid connector 210a and prevent ambient light from outside the device 2 affecting the measurement of fluorescence after the sample 1 has been poured into the chamber 70 through the top plate 160. The upper portion of the walls of the chamber 70 are chamfered to receive the funnel insert, and the upper fluid connector 210a penetrates the upper portion of one of the walls of the chamber 70. The sample 1 drains through the lower fluid connector 210b, which is fitted with a tap (or valve) 215 to control liquid flow. A separate light-tight cap 216 may optionally be provided at the upper fluid connector 210a and/or the lower fluid connector 210b to further eliminate interference from ambient light when the device 2 operates in discrete-sample mode.

In other embodiments, the blocking member 195 is in the form of a hollow funnel through which a sample 1 can be poured. A separate light-tight cap is provided for covering the blocking member when a measurement is being taken.

In flow-through mode (FIG. 6b) the blocking member 195 is removed and a blocking member 190 in the form of a funnel insert having a flow path through it is screwed in place to fluidly connect the top of the chamber 70 to the upper fluid connector 210a. The tap 215 is opened to allow water to flow through the lower fluid connector 210b. This results in a continuous flow path from the outside of the case 220, through the lower fluid connector 210b, through the chamber 70 and out of the case 220 through the upper fluid connector 210a. The blocking member 190 prevents ambient light from entering the chamber 70. It would be readily understood that the flow of ballast water can be reversed, so that in flow-through mode, the sample 1 enters the chamber 70 via the upper fluid connector 210a.

FIGS. 6a and 6b are not drawn to scale in order to improve clarity. In reality, the flow path between the bottom of the chamber 70 and the tap 215 is relatively small compared to the volume of the chamber 70. The chamber 70 typically holds a sample 1 size of 20 mL. The interrogated volume is typically 0.5 mL. In other words, the interrogated volume is typically about 2.5% of the sample volume.

In further embodiments, an opaque cap, such as a screw-on cap or a push-on cap, is removably installed on the top of the chamber 70 to prevent ambient light from entering the chamber 70 when a measurement is taken. The tap 215 on the lower fluid connector 210b is controlled to allow or prevent the sample from entering the chamber 70, or in other words, to allow or prevent flow-through mode. When the flow-through mode is prevented, the ballast water monitoring device 2 operates in discrete-sample mode. A tap on the upper fluid connector 210a is controllable to prevent any of the sample 1 escaping the chamber 70. The light-tight cap 216 may be provided alternatively or in addition to the tap on the upper fluid connector 210a. In these embodiments, the tap(s) 215 function as blocking members. In other words, this arrangement allows the cell counting device 2 to quickly switch between flow-through and discrete-sample modes by controlling the valves 215, 218, without changing the blocking member 190, 195. This is particularly useful when the cell counting device 2 is integrated with a vessel. This hybrid mode is called stop-start mode.

FIGS. 7a and 7b show alternative arrangements of the blocking members 190, 195 and chamber 70 described with reference to FIGS. 6a and 6b. In FIG. 7a, the blocking member 195 is a rectangular housing having a screw-thread for attaching it to the chamber 70, which has a square top. A funnel insert is provided within the housing, which functions similarly to that described with reference to FIG. 6a. In FIG. 7b, the blocking member 190 is in the form of a rectangular housing having a flow path arranged therein, similarly to the blocking member 190 described with reference to FIG. 6b. The blocking member 190 is screw-threaded, but it would be appreciated that it may be secured using friction or a clamp. In FIGS. 7a and 7b, the upper fluid connector 210a does not penetrate a wall of the chamber 70; instead, the blocking member 190 fluidly connects the upper fluid connector 210a to the chamber 70. Light-tight caps 216 may be provided to cover the upper and lower fluid connectors 210a, 210b when the device 2 operates in discrete-sample mode. The upper surface of the blocking members 190, 195 prevents light from entering the chamber 70.

Figure 8:
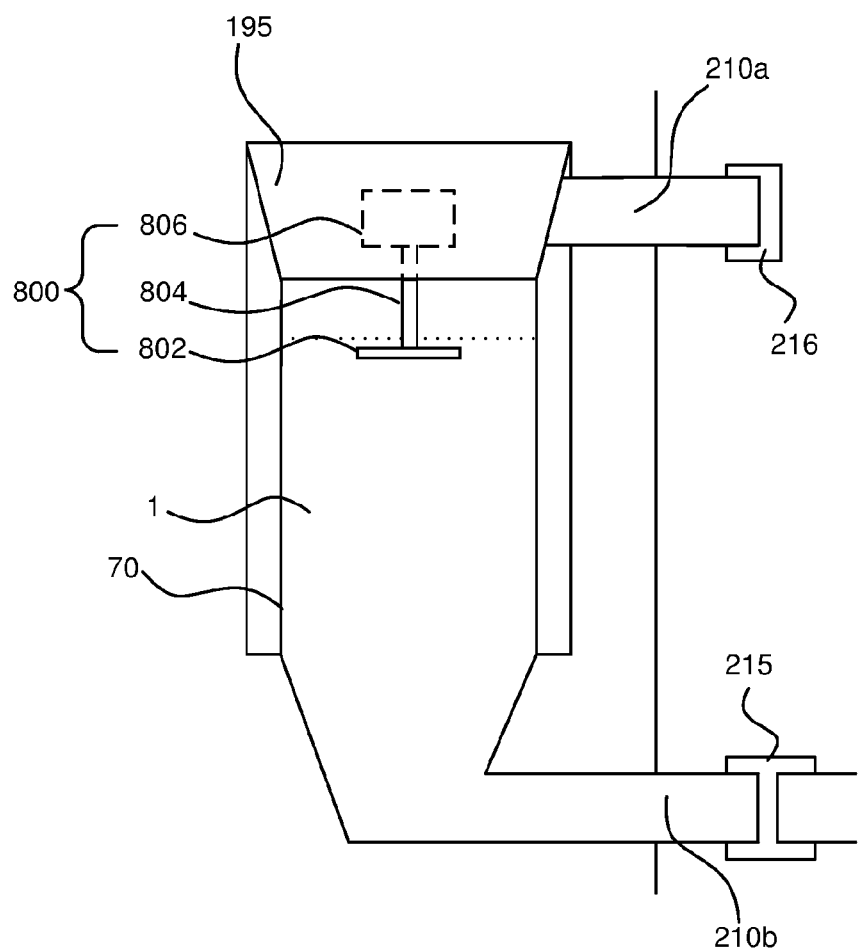
FIG. 8 shows a cross section of a ballast water monitoring device operating in discrete-sampling mode, according to an embodiment of the ballast water monitoring device of the invention.

FIG. 8 relates to a more specific example of a blocking member 195 used when the ballast water monitoring device 2 is operating in discrete-sample mode. Here, a stirrer 800 is integrated with the blocking member 195. One end of the stirrer 800 is an elongate horizontal member 802 arranged to extend into the sample 1 when the sample 1 is in the chamber 70. The stirrer 800 also includes a shaft 804 for coupling the elongate horizontal member 802 to a motor 806.

The motor 806 rotates the shaft at a frequency of between about 1 Hz and about 20 Hz. Typically, the stirrer 800 operates at 2 Hz. To control the frequency of rotation, the motor 806 may include a gearbox. For example, the gearbox may be a 60:1 gearbox. The motor 806 may be powered by an external power supply, or may be electrically coupled to the power supply 10 of the ballast water monitoring device 2.

The blocking member 195 having the integrated stirrer 800 may have electrical contacts that electrically couple to corresponding electrical contacts arranged around the mouth of the chamber 70. Therefore, when the blocking member 195 is inserted into the chamber 70, the motor 806 is supplied with power from the power supply 10. The motor 806 may be automatically activated, or may be activated by means of a manual switch.

Alternatively to an elongate horizontal member 802, the shaft 804 of the stirrer 800 may be coupled to a flat plate, a blade, or a whisk. In other words, the stirrer 800 may comprise any suitable means for mixing the sample 1 so that a subsample within the interrogated volume opposite the light detector 40 is exchanged with the rest of the sample 1.

The stirrer 800 may be integrated with the side wall of the chamber 70, such that the blocking members 195, 190 shown in FIGS. 6a and 6b, and in the other described embodiments, can be used without further modification.

Figure 9:
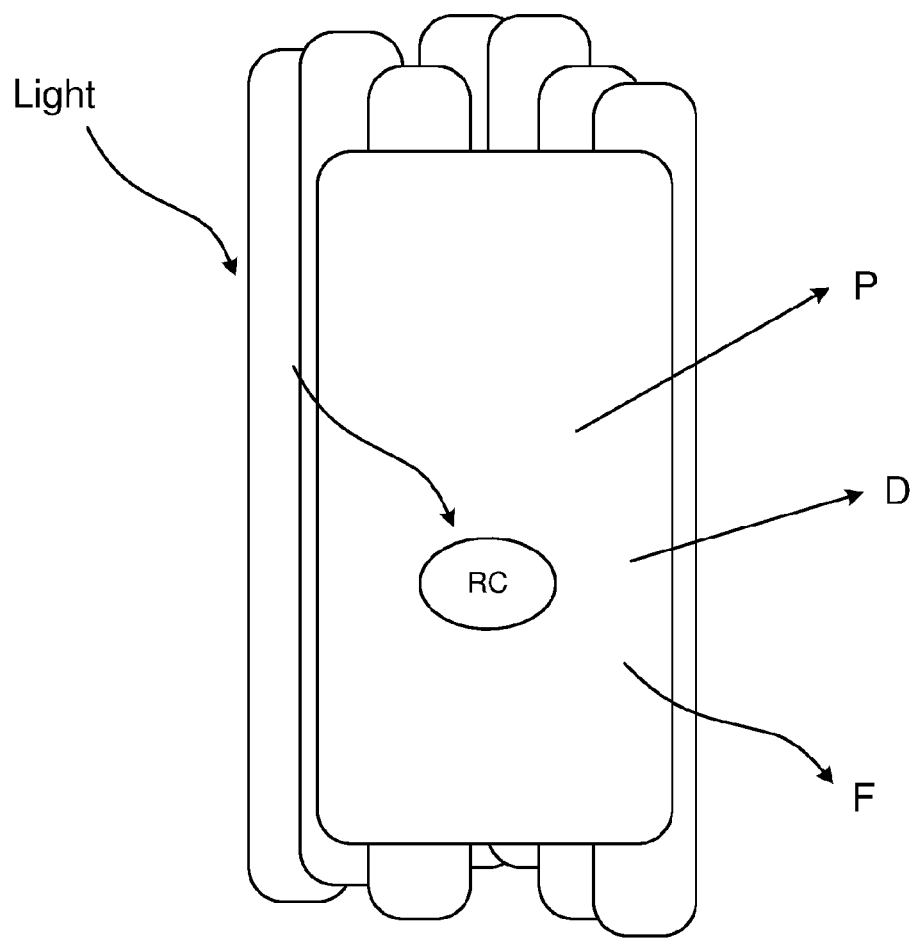
FIG. 9 shows a schematic diagram of a phytoplankton's response to light.

FIG. 9 shows the processes that occur within phytoplankton in order to cause detectable fluorescence. Dead phytoplankton cannot photosynthesise; however, they may emit some detectable fluorescence (F) when exposed to light. The emission from dead phytoplankton is not a time-dependent response. This residual emission is a component of the minimal fluorescence ($F_0$).

In live phytoplankton, light absorbed by the Light Harvesting Complex is rapidly transferred to a Chlorophyll-a molecule associated with the Reaction Centre RC in Photosystem II (PSII), located in the thylakoid membrane of the phytoplankton. The cycle of photochemistry is then initiated, and the Reaction Centre remains closed for approximately 200 µs. While closed, the Reaction Centre cannot utilize any more of the light energy that is absorbed. A proportion of the excess energy is emitted as additional fluorescence F which is monitored using the present invention.

FIGS. 10a and 10b show a detection method according to a prior art device. Here, the light source is a single LED emitting light having a wavelength of 470 nm. The vertical lines on graphs represent individual 'Flashlets', each 1 µs in duration. During saturation phase, one hundred Flashlets spaced apart by a 1 µs interval are used to saturate the sample 1. Saturation means that all Reaction Centres in the sample 1 are closed. This is referred to as a 'single turnover measurement'.

As a proportion of the Reaction Centres close with each Flashlet, the fluorescence signal detected increases until saturation occurs. Fluorescence measurements are recorded while the LED is on and then again when it is switched off. This enables background ambient light and non-variable fluorescence ($F_0$) to be subtracted from the measurement ($F_m$) so only the induced variable fluorescence ($F_v$) is detected.

During the Relaxation Phase, the interval between Flashlets is increased to about 50 µs to allow some of the Reaction Centres to reopen. The shape of the relaxation response provides information about the downstream electron transfer processes between PSII and Photosystem I (PSI) that occur on a longer timescales.

FIGS. 11a and 11b show a detection technique according to an embodiment of the present invention. Here, multiple wavelength excitation is provided, as described with reference to FIG. 2. In adapting the detection technique for ballast water monitoring it was necessary to maximise measurement sensitivity, as the detection limits required to meet the IMO D2 Standard (10-50 µm) and the US Coast Guard Discharge Standard (10-50 µm) are very low.

As the ballast water measurement is typically performed in the dark, it was discovered that it is not necessary to pulse the light source to provide ambient light subtraction.

With a single turnover approach, PSII rapidly returns to the 'dark adapted' state, typically within a few milliseconds, enabling flash sequences to be repeated rapidly to build up good signal to noise ratios. This feature of the measurement technique not only provides good sensitivity but also allows measurements to be performed in moving water, which is not possible with 'multiple turnover' techniques according to FIGS. 10a and 10b where it can take many seconds for PSII to recover to the 'dark adapted' state.

According to an embodiment, a single 400 µs pulse of light is used to saturate PSII. This means that at least twice as many fluorescence measurements can be performed within a single flash sequence when compared to the prior art device, which improves the signal to noise by a factor of at least $\sqrt{2}$.

Measurement sequences are repeated until a statistical discrimination of any variable fluorescence is achieved. In practice, it has been shown that any detection of variable fluorescence in the sample 1 indicates non-compliance, so no reference to instrument calibrations against know algal species is required.

As shown in FIG. 11b, as a result of the single continuous pulse of light, a time-dependent response from the phytoplankton is measurable. The response is measured at time intervals much less than the duration of the pulse of light. Where the fluorescence peaks is determined to be $F_m$. $F_0$ is calculated using regression analysis. $F_0$ is taken away from $F_m$ to provide $F_v$.

In more detail, $F_0$ is calculated as follows. Linear regression through the first 60 points (at one microsecond a point) is applied. The results from this 60 point regression (slope, intercept and standard error) are set as reference values. The number of points in the regression is then decreased, in steps of 2, down to 20 points. If the slope is higher and the standard error is lower at any step, the results from that step become the reference values. $F_0$ is calculated through extrapolation of the final reference regression line to zero time. The slope of the increase in fluorescence decreases between $F_0$ and $F_m$, even over the first few microseconds. Consequently, the shorter the regression line, the better the fit. The requirement for a lower standard error imposes a quality check. If the signal to noise is high, the reference regression line is at or close to 20 points.

To calculate $F_m$ linear regression through the last 240 points (at one microsecond a point) is applied. If the slope is positive (still increasing) or flat, $F_m$ is set by extrapolating to the end of the pulse. If the slope is negative (starting to decrease), $F_m$ is set by extrapolating to the start of the pulse. If the slope is positive, saturation has not been reached. Consequently, the extrapolation should be to the end of the pulse. A negative slope is indicative of known artefacts, which quenches $F_m$ from the maximum level. Extensive testing has shown that extrapolating to the start of the pulse minimises the error generated by this quenching.

The phytoplankton enters the Relaxation Phase when the light pulse is switched off, although this does not form part of the process for determining whether phytoplankton are present in the sample 1 according to embodiments of the invention.

FIGS. 12a-d show examples of fluorescence induction spectra for different algal species, specifically *Ulva* sp., *Porphyridium cruentum*, *Chaetoeros gracilis*, and *Chroomonas* sp. As can be seen by comparing these Figures, different algal species absorb light at a range of wavelengths. For example blue excitation light, having a wavelength of 470 nm, might result in the detection of diatoms that have high levels of chlorophyll pigments, but would not excite marine cyanobacteria that have low levels of chlorophyll and predominantly absorb light in the green region of the spectrum. Therefore, as previously described, multiple wavelength excitation is used to ensure that all phytoplankton groups within the sample 1 are detected.

Figure 12A:
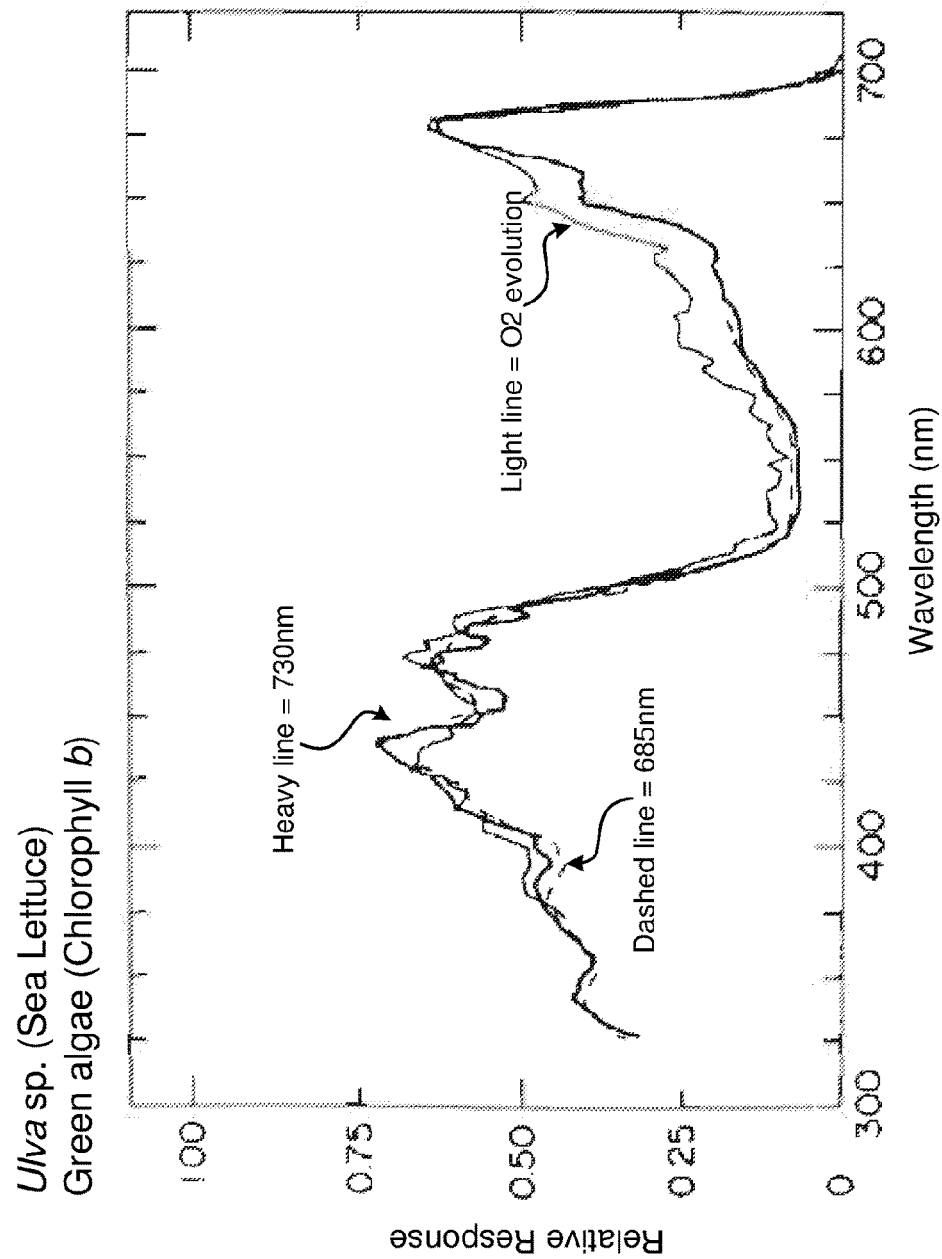
FIGS. 12a to 12f show emission profiles for different phytoplankton species.
Figure 12B:
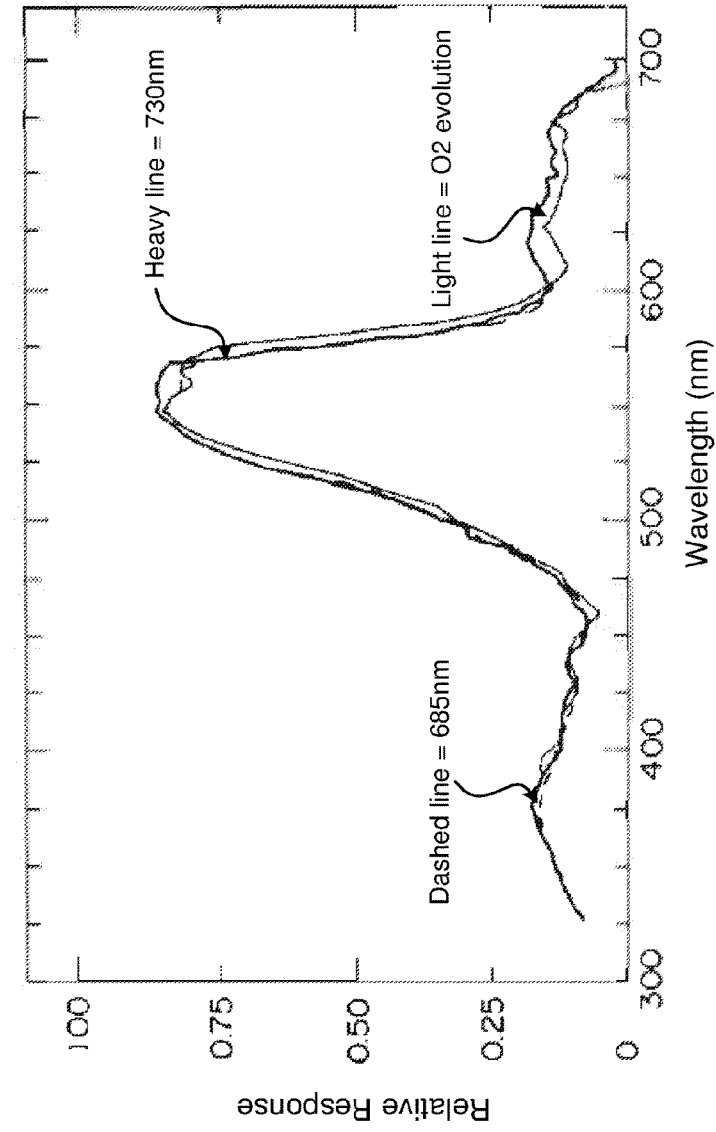
Figure 12C:
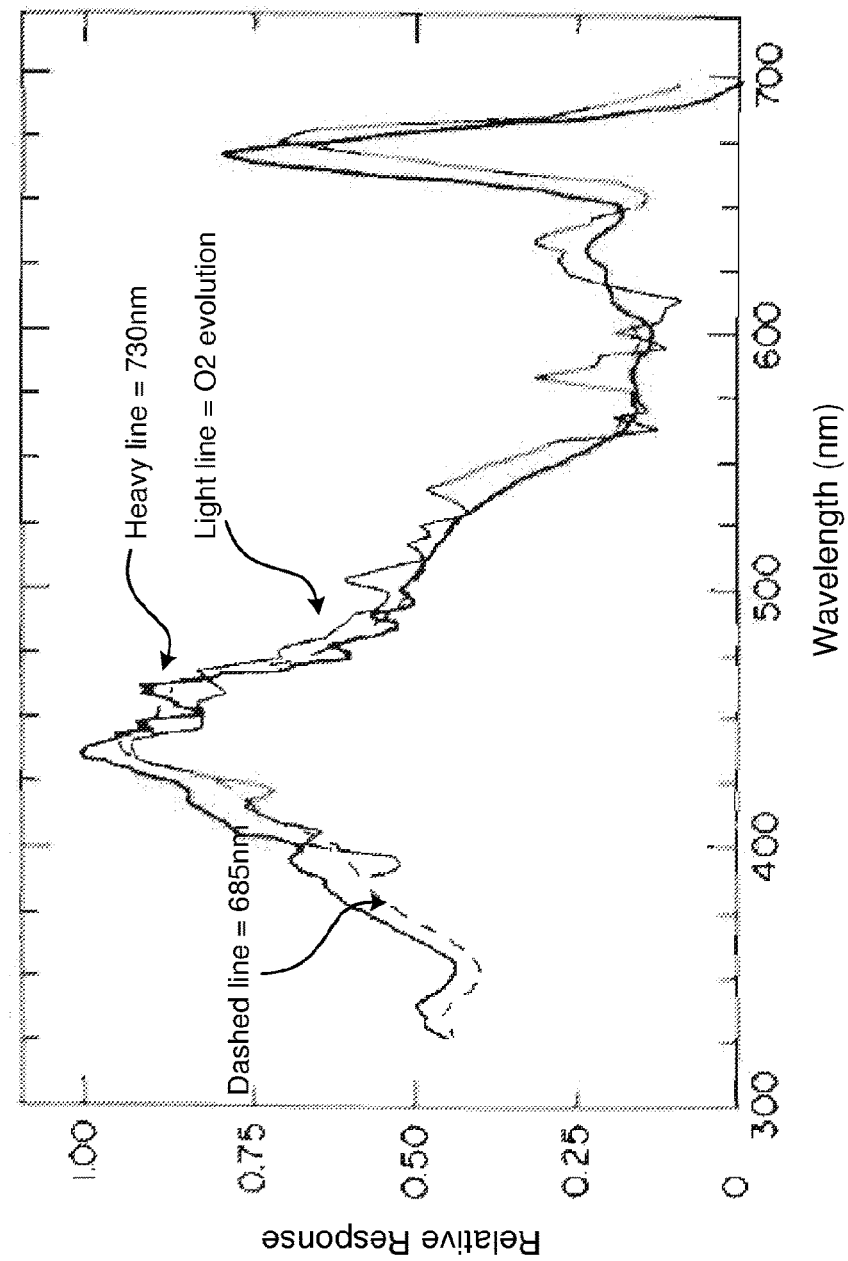
Figure 12D:
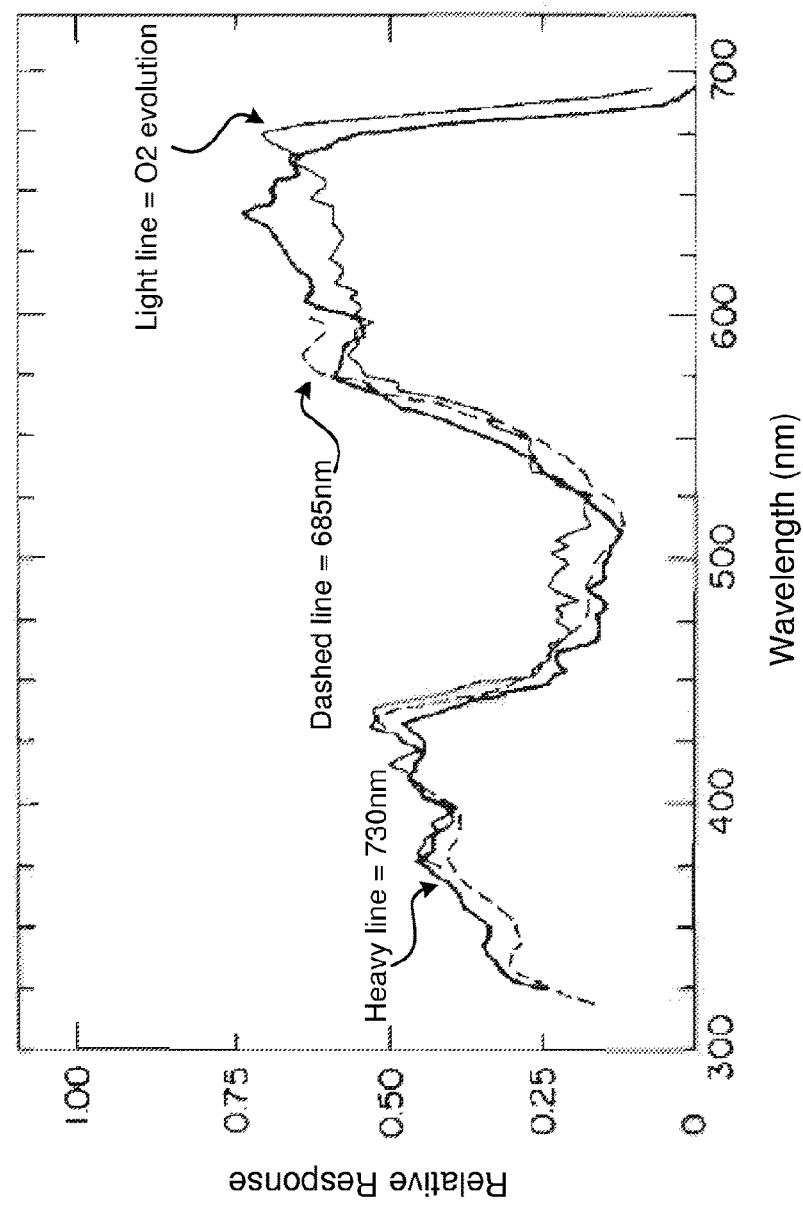
Figure 12E:
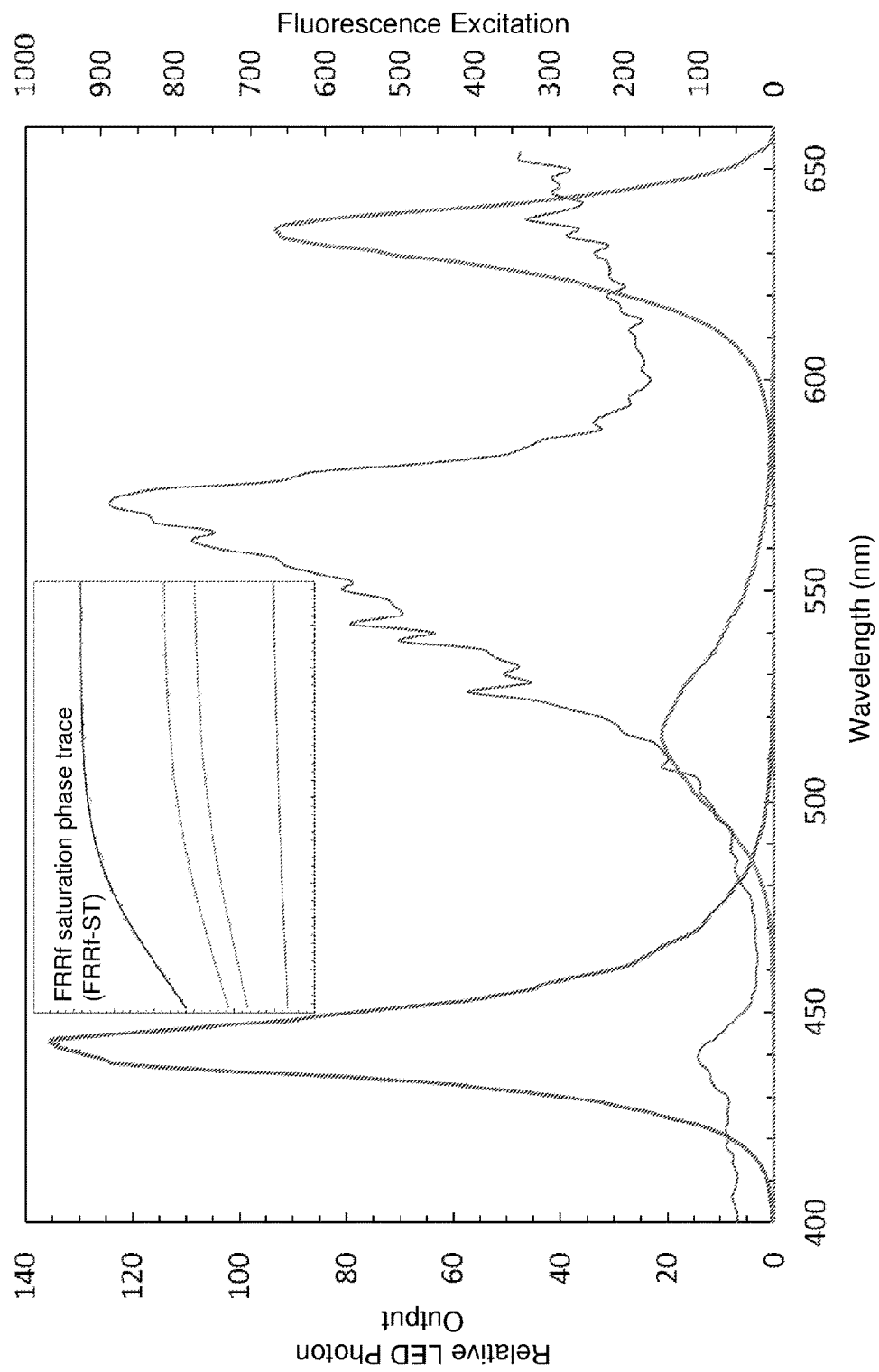
Figure 12F:
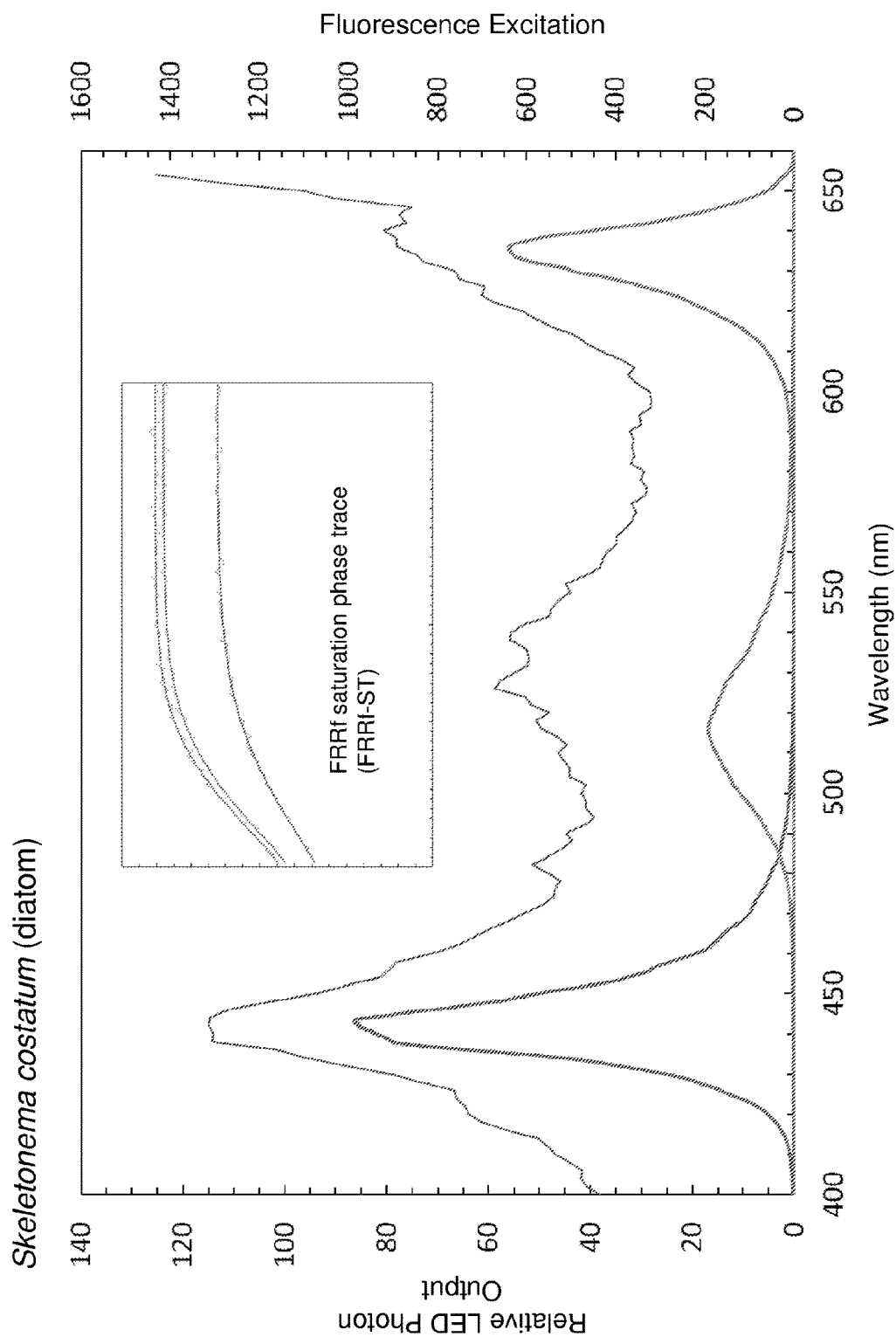

FIGS. 12e and 12f show the overlap between the emission spectra of the light sources within the light source array 50 of the ballast water monitoring device 2. More specifically, the graphs show a plot of wavelength against relative LED photon output and fluorescence excitation, which are both on a relative scale. The insets within FIGS. 12e and 12f show the level of $F_v$ generated by different combinations of light sources.

Figure 13:
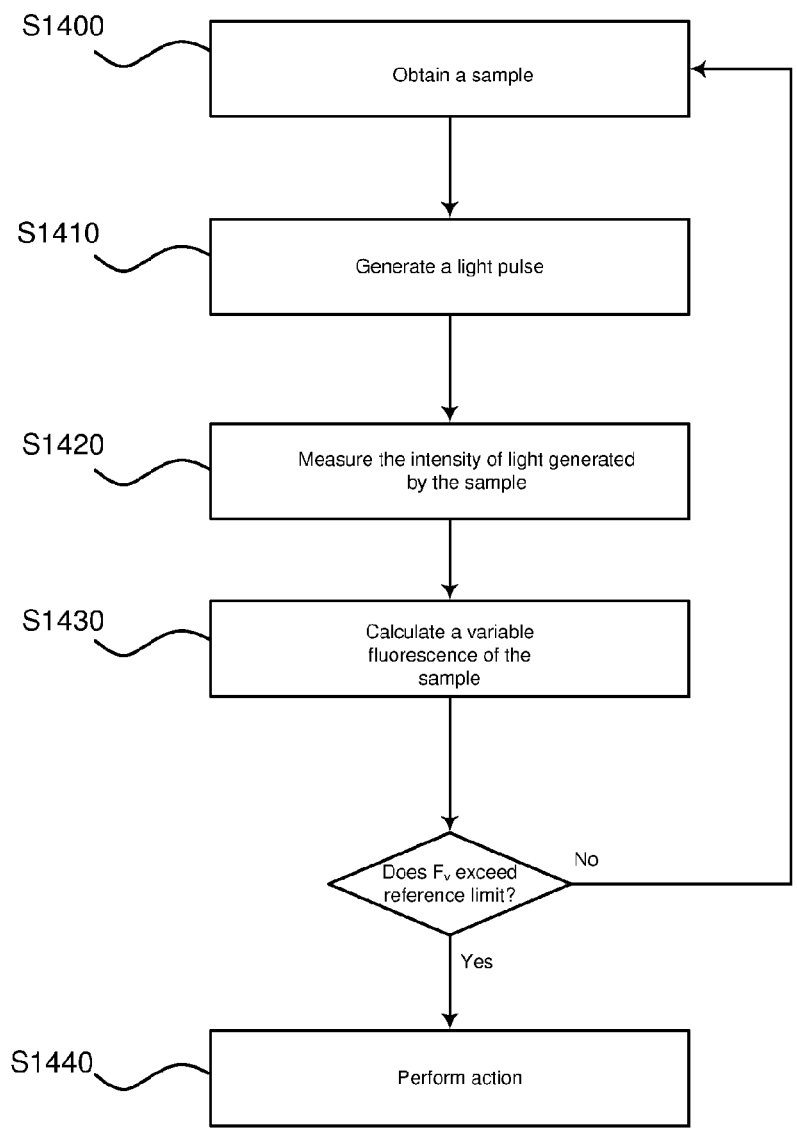
FIG. 13 shows a flowchart of a ballast monitoring process according to an embodiment of the present invention.

FIG. 13 shows a method of detecting live phytoplankton suspended in ballast water. In a first step S1400, a sample 1 is obtained. A sample 1 is, for example, ballast water in the hull of a waterborne vessel. The ballast water monitoring device 2 may be configured in discrete-sample mode, or flow-through mode. In flow-through mode, samples 1 continuously and automatically enter and exit the chamber 70.

At step 1410, a pulse of light is generated and directed towards the sample 1. The pulse of light, according to some embodiments, is generated using a plurality of light sources 52 and comprises light having a plurality of wavelengths. The pulse of light has a duration of between 200 and 500 µs, with a PRF of between 10 and 50 Hz. Typically, the pulse of light has a duration of 400 µs and a PRF of 40 Hz. The pulse of light is projected onto the sample 1 using lenses so that a uniform light field is spread across the sample 1. For example, one of the lenses is an achromatic doublet lens 100 to direct light of multiple wavelengths into the chamber 70 such that the sample 1 is illuminated with a uniform light field. In other embodiments, the plurality of light sources 52, producing light of different wavelengths, are located on a curved surface such that the sample 1 is illuminated with a uniform light field.

At step 1420, the intensity of the light generated by the sample 1 in response to being illuminated by the pulse of light is measured. The intensity is measured at time intervals less than the duration of the pulse of light. For example, the intensity is measured at 1 µs intervals, before, during and after the pulse of light is emitted.

The variable fluorescence ($F_v$) of the sample 1 is calculated at step S1430. In some embodiments, this is achieved using the method as previously described. Calculating $F_v$ involves estimating a minimal fluorescence ($F_0$) of the sample using linear regression, and subtracting that value from the maximal fluorescence ($F_m$).

If the calculated value of $F_v$ exceeds a predetermined reference limit, at step S1440 an action is performed. The action may be indicating that the sample 1 is not compliant with the IMO D2 Standard (10-50 µm) and the US Coast Guard Discharge Standard (10-50 µm), using the display 60, an indicator light or an audible alarm if the variable fluorescence exceeds the reference limit. Alternatively, the action may be controlling a means for exterminating live phytoplankton cells, such as a ballast water treatment system.

In further embodiments, steps S1410-S1430 are repeated a number of times, such that the same sample 1 undergoes a number of interrogations. The calculated values of $F_v$ are then divided by the number of interrogations to give an average value of $F_v$ for the sample 1. The sample 1 may be stirred using the stirrer 800 between each interrogation. This ensures that all liquid within the sample 1 enters the interrogated volume, or the region opposite the light detector 40, at some point during the test. For example, the sample 1 is stirred at a speed that provides an optimum rate of subsample exchange with the sample 1. The speed of rotation of the stirrer 800 may be between 1 Hz and 20 Hz. Typically, the stirrer 800 operates at 2 Hz.

Figure 14:
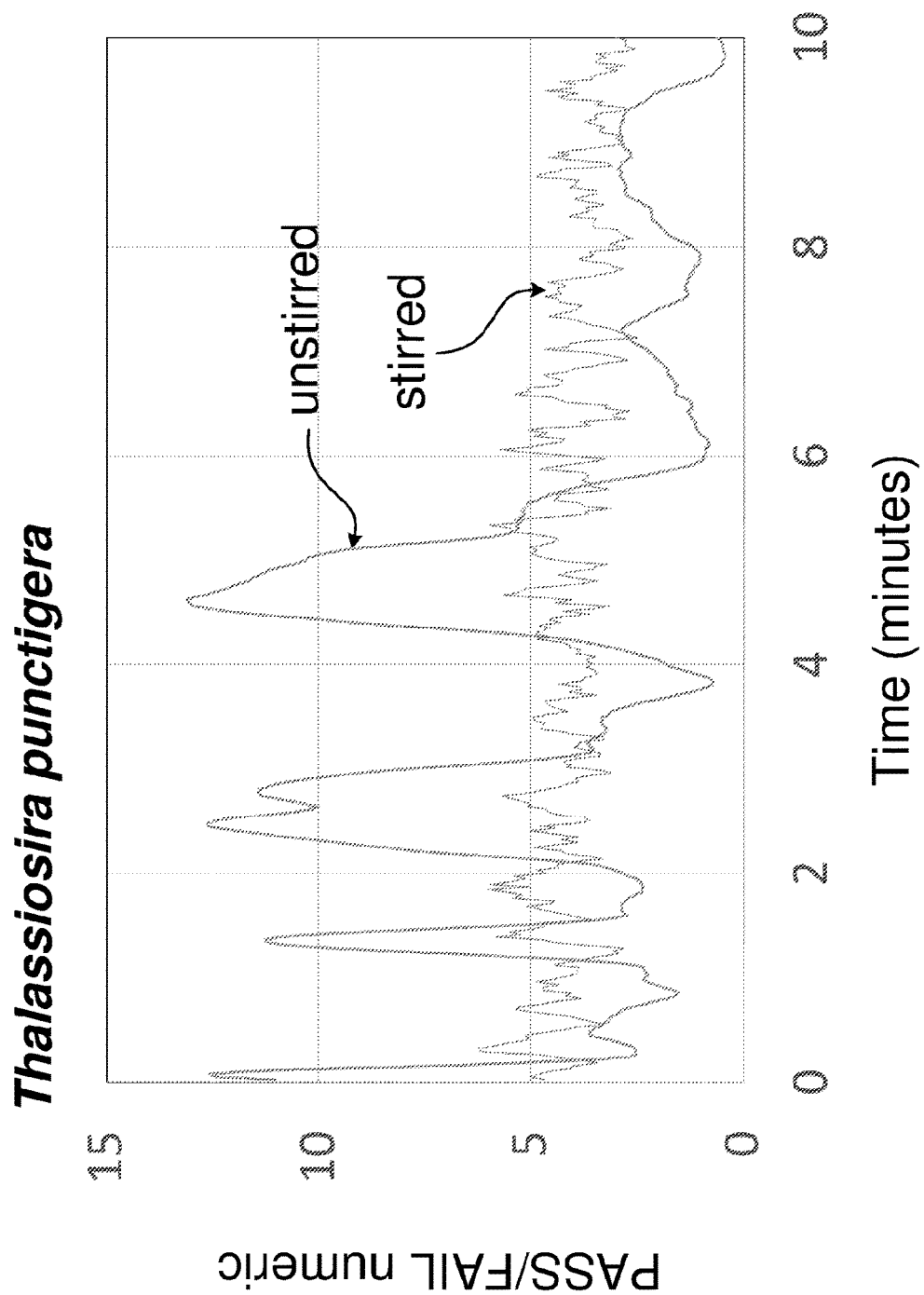
FIG. 14 is a graph that shows the effect of stirring the sample.

The effect of stirring the sample 1 is evident from FIG. 14. Here, it is clear that stirring the sample 1 reduces the variability of the measurements of $F_v$, and consequently a more accurate result can be measured. A sharp peak in $F_v$ may occur when a colony of phytoplankton enter the interrogation region, giving the impression that the sample 1 has a high cell density. By mixing the sample 1, the colony is broken up, and the cell density across the sample 1 as a whole is made more homogenous.

Advantages of the ballast water monitoring device 2 reside in the provision of the processor 20 for applying an algorithm to determine the presence of phytoplankton. This allows for an improved signal to noise ratio, and allows the device to be operated on moving ballast water.

Although a few exemplary embodiments have been shown and described, it will be appreciated by those skilled in the art that changes may be made in these exemplary embodiments without departing from the principles of the invention, the range of which is defined in the appended claims.

The invention claimed is:

1. A ballast water monitoring device for detecting live phytoplankton, the device comprising:
   a chamber for receiving a sample;
   at least one light source to emit light towards the sample;
   a light detector to receive light from the sample and generate a light signal; and
   a controller configured to:
      control the at least one light source to emit a single pulse of light with a duration of up to 450 µs,
      calculate the variable fluorescence [$F_v$] of the sample in response to the pulse of light, at time intervals less than the duration of the pulse of light,
      compare the calculated variable fluorescence to a predetermined reference limit, and
      perform an action when the calculated variable fluorescence is greater than the predetermined reference limit.

2. The ballast water monitoring device of claim 1, comprising a plurality of light sources, wherein each light source is associated with a different wavelength.

3. The ballast water monitoring device of claim 1, further comprising an indicator, for indicating to the user that the variable fluorescence exceeds the predetermined reference limit, wherein performing an action comprises activating the indicator.

4. The ballast water monitoring device according to claim 1, wherein the pulse of light has a duration of greater than 100 µs, or greater than 200 µs, or greater than 300 µs, or between 350 µs and 450 µs, or between 390 µs and 410 µs.

5. The ballast water monitoring device according to claim 1, wherein the pulse of light has a duration of about 400 µs.

6. The ballast water monitoring device according to claim 1, wherein the controller is configured to measure the variable fluorescence by measuring the intensity of the received light at intervals of between 0.1 µs and 10 µs, or between 0.2 and 8 µs, or between 0.5 and 5 µs, or between 0.8 and 3 µs.

7. The ballast water monitoring device according to claim 1, wherein the controller is configured to measure the variable fluorescence by measuring the intensity of the received light at about 1 µs intervals.

8. The ballast water monitoring device according to claim 1, wherein the at least one light source is configured to emit light having a wavelength of one of about 450 nm, 470 nm, 530 nm and 624 nm, wherein when there are a plurality of light sources, the plurality of light sources are configured to emit light having wavelengths of at least two of about 450 nm, 470 nm, 530 nm and 624 nm simultaneously.

9. The ballast water monitoring device according to claim 1, wherein the chamber comprises an inlet and an outlet, through which water can continuously flow, wherein the chamber comprises a removable blocking member for blocking the inlet or the outlet to allow a discrete sample to be measured, wherein at least one valve arranged in the inlet or the outlet to block the inlet or the outlet to allow a discrete sample to be measured and wherein the blocking member comprises a stirrer for stirring the sample.

10. The ballast water monitoring device according to claim 1, further comprising a plurality of lenses configured to generate a uniform light field directed into the chamber, wherein at least one of the plurality of lenses is an achromatic doublet lens, wherein the plurality of lenses comprise an array of plano-convex lenses positioned directly in front of the plurality of light sources and wherein when the plurality of lenses comprise an array of plano-convex lenses positioned directly in front of the plurality of light sources, the plurality of lenses comprise a shortpass filter placed in front of the array of plano-convex lenses.

11. The ballast water monitoring device according to claim 1, wherein the controller is configured to estimate a minimal fluorescence [$F_0$] of the sample using regression analysis, and subtract that value from the maximal fluorescence [$F_m$] to provide $F_v$, wherein the controller is configured to estimate $F_0$ of the sample using regression analysis of a first part of the generated light signal, estimate $F_m$ of the sample using regression analysis of a second part of the generated light signal, and subtract $F_0$ from $F_m$ to provide $F_v$.

12. The ballast water monitoring device according to claim 1, wherein the controller is further configured to repeat the steps of:
controlling the at least one light source to emit a single pulse of light; and
calculating the variable fluorescence [$F_v$] of the sample in response to the pulse of light, at time intervals less than the duration of the pulse of light, and the controller being further configured to:
average the calculated variable fluorescence over the number of repetitions; and
perform the action when the average calculated variable fluorescence is greater than the predetermined reference limit.

13. The ballast water monitoring device according to claim 1, wherein the ballast water monitoring device further comprises a stirrer for stirring the sample, wherein the stirrer is arranged to pass through a side wall of the chamber.

14. A system comprising:
a ballast water treatment system; and
a ballast water monitoring device comprising:
a chamber for receiving a sample;
at least one light source to emit light towards the sample;
a light detector to receive light from the sample and generate a light signal; and
a controller configured to:
control the at least one light source to emit a single pulse of light with a duration of up to 450 μs,
calculate the variable fluorescence [Fv] of the sample in response to the pulse of light, at time intervals less than the duration of the pulse of light,
compare the calculated variable fluorescence to a predetermined reference limit, and
when the calculated variable fluorescence is greater than the predetermined reference limit the ballast water monitoring device controls the ballast water treatment system to eliminate live phytoplankton cells.

15. A method of determining whether live phytoplankton are present in a sample, the method comprising:
generating a pulse of light with a duration of up to 450 μs and directing it towards the sample;
receiving a light from the sample in response to receiving the pulse of light, and generating a light signal;
calculating the variable fluorescence [$F_v$] of the sample in response to receiving the pulse of light at time intervals less than the duration of the pulse of light;
comparing the calculated variable fluorescence to a predetermined reference limit; and
performing an action when the calculated variable fluorescence exceeds the predetermined reference limit.

16. The method of claim 15, wherein generating the pulse of light comprises activating a plurality of light sources, wherein performing the action comprises indicating that the variable fluorescence exceeds the predetermined reference limit and wherein the performing the action comprises controlling a means for exterminating live phytoplankton cells.

17. The method according to claim 15, wherein the pulse of light has a duration of greater than 200 μs, or greater than 300 μs, or between 350 μs and 450 μs, or between 390 μs and 410 μs, or about 400 μs; and the method comprising calculating the variable fluorescence by measuring the intensity of the generated light signal at intervals of between 0.1 μs and 10 μs, or between 0.2 and 8 μs, or between 0.5 and 5 μs, or between 0.8 and 3 μs.

18. The method of according to claim 15, wherein the pulse of light comprises light having a wavelength of one of about 450 nm, 470 nm, 530 nm and 624 nm, wherein when a plurality of light sources are activated, the pulse of light comprises light having wavelengths of at least two of about 450 nm, 470 nm, 530 nm and 624 nm.

19. The method according to claim 15, comprising generating a uniform light field and directing it into a chamber in which the sample is contained.

20. The method according to claim 15, comprising estimating a minimal fluorescence [$F_0$] of the sample using regression analysis, and subtracting that value from the maximal fluorescence [$F_m$] to provide $F_v$, wherein estimating $F_0$ of the sample using regression analysis of a first part of the generated light signal, estimating $F_m$ of the sample using regression analysis of a second part of the generated light signal, and subtracting $F_0$ from $F_m$ to provide $F_v$.

* * * * *